(12) United States Patent
Lane et al.

(10) Patent No.: US 12,085,963 B2
(45) Date of Patent: Sep. 10, 2024

(54) SYSTEMS, APPARATUS, AND METHODS FOR REDUCING FLUID PRESSURE IN A FLUID LINE

(71) Applicant: 410 Medical, Inc., Durham, NC (US)

(72) Inventors: Andrew Lane, Rolesville, NC (US); Savannah K. Steele, Durham, NC (US); Galen C. Robertson, Apex, NC (US); Mark D. Piehl, Chapel Hill, NC (US); Stephen Latham, Sun Prairie, WI (US); Douglas Rodenkirch, Sun Prairie, WI (US); Jesse Darley, Madison, WI (US); Curtis Irwin, Madison, WI (US); Amrish Chourasia, Beloit, WI (US)

(73) Assignee: 410 Medical, Inc., Researh Triangle Park, NC (US)

( * ) Notice: Subject to any disclaimer, the term of this patent is extended or adjusted under 35 U.S.C. 154(b) by 474 days.

(21) Appl. No.: 17/129,107

(22) Filed: Dec. 21, 2020

(65) Prior Publication Data

US 2021/0325916 A1    Oct. 21, 2021

Related U.S. Application Data

(63) Continuation of application No. 16/539,569, filed on Aug. 13, 2019, now Pat. No. 10,871,788.
(Continued)

(51) Int. Cl.
*G05D 16/06* (2006.01)
*A61M 39/22* (2006.01)

(52) U.S. Cl.
CPC ......... *G05D 16/0655* (2013.01); *A61M 39/22* (2013.01); *A61M 2205/3334* (2013.01)

(58) Field of Classification Search
CPC .......... A61M 2205/3334; A61M 39/22; A61M 2205/3379; A61M 2206/22;
(Continued)

(56) References Cited

U.S. PATENT DOCUMENTS

| 4,623,335 A | 11/1986 | Jackson |
| 4,741,733 A | 5/1988 | Winchell et al. |

(Continued)

FOREIGN PATENT DOCUMENTS

| WO | WO 2014/145354 A1 | 9/2014 |
| WO | WO 2016/138018 | 9/2016 |
| WO | WO-2020036964 A1 | 2/2020 |

OTHER PUBLICATIONS

Extended European Search Report, dated Apr. 11, 2022, for EP Application No. 19849310.8 (14 total pages).
(Continued)

*Primary Examiner* — Brandy S Lee
(74) *Attorney, Agent, or Firm* — COOLEY LLP

(57) ABSTRACT

In some embodiments, a tube portion can be configured to be fluidically coupled to a patient access component. A source of pressurized fluid can be coupled to the tube portion and can be configured to deliver fluid to the tube portion at a source pressure. A fluid pressure regulating device can include an expandable reservoir and can be coupled to the tube portion such that the expandable reservoir is in fluidic communication with the tube portion. The fluid pressure regulating device can be configured such that, when fluid is delivered from the source of pressurized fluid to the lumen of the tube portion at the source pressure, the expandable reservoir of the fluid pressure regulating device can receive fluid such that the expandable reservoir of the fluid pressure
(Continued)

regulating device expands and fluid is delivered from the lumen of the tube portion to the patient via the patient access component.

20 Claims, 17 Drawing Sheets

Related U.S. Application Data

(60) Provisional application No. 62/718,139, filed on Aug. 13, 2018.

(58) Field of Classification Search
CPC .. A61M 5/1452; A61M 5/16877; A61M 5/48; A61M 5/484; G05D 16/0655
See application file for complete search history.

(56) References Cited

U.S. PATENT DOCUMENTS

| | | | |
|---|---|---|---|
| 4,968,301 A | 11/1990 | di Palma et al. | |
| 4,998,918 A | 3/1991 | Mimura | |
| 5,211,632 A | 5/1993 | Tsukada | |
| 5,263,940 A | 11/1993 | Kriesel | |
| 5,284,481 A | 2/1994 | Soika et al. | |
| 5,306,257 A | 4/1994 | Zdeb | |
| 5,807,340 A | 9/1998 | Pokras | |
| 5,897,530 A | 4/1999 | Jackson | |
| 7,220,245 B2 | 5/2007 | Kriesel | |
| 7,828,770 B2 | 11/2010 | Bivin et al. | |
| 8,083,717 B2 | 12/2011 | Kriesel | |
| 8,162,878 B2 | 4/2012 | Bonnette et al. | |
| 8,292,848 B2 | 10/2012 | Kriesel et al. | |
| 8,672,990 B2 | 3/2014 | Holman et al. | |
| 8,968,242 B2 | 3/2015 | Tefera et al. | |
| 9,506,479 B1 | 11/2016 | Theobald | |
| 9,526,641 B2 | 12/2016 | Irwin et al. | |
| 10,010,673 B2 | 7/2018 | Burns et al. | |
| 10,016,564 B2 | 7/2018 | Piehl et al. | |
| 10,322,227 B2 | 6/2019 | Piehl et al. | |
| 10,391,257 B2 | 8/2019 | Piehl et al. | |
| 10,871,788 B2 * | 12/2020 | Lane | A61M 5/48 |
| 11,458,256 B2 | 10/2022 | Piehl et al. | |
| 2001/0039397 A1 | 11/2001 | Kriesell et al. | |
| 2005/0277882 A1 | 12/2005 | Kriesel | |
| 2007/0078369 A1 | 4/2007 | Tamari | |
| 2011/0282197 A1 | 11/2011 | Martz | |
| 2013/0345633 A1 | 12/2013 | Chong | |
| 2015/0025500 A1 | 1/2015 | Piehl et al. | |
| 2015/0202361 A1 | 7/2015 | Burns et al. | |
| 2016/0106915 A1 * | 4/2016 | Burns | F16K 17/048 604/247 |
| 2016/0166761 A1 | 6/2016 | Piehl et al. | |
| 2016/0317738 A1 | 11/2016 | Cross et al. | |
| 2016/0339169 A1 | 11/2016 | Hauswald | |
| 2017/0281875 A1 | 10/2017 | Piehl et al. | |
| 2017/0319783 A1 | 11/2017 | Piehl et al. | |
| 2018/0185576 A1 | 7/2018 | Burns et al. | |
| 2020/0050222 A1 | 2/2020 | Lane et al. | |
| 2023/0144057 A1 | 5/2023 | Piehl et al. | |

OTHER PUBLICATIONS

International Search Report and Written Opinion issued in International Application No. PCT/US2019/046359 on Oct. 17, 2019, 13 pages.

Non-Final Office Action issued by the United States Patent and Trademark Office for U.S. Appl. No. 16/539,569, dated Oct. 25, 2019, 17 pages.

Final Office Action, dated Apr. 30, 2020, for U.S. Appl. No. 16/539,569, 15 pages.

International Preliminary Report on Patentability, mailed Feb. 25, 2021, for International Application No. PCT/US2019/046359, 12 pages.

Notice of Allowance, mailed Aug. 18, 2020, for U.S. Appl. No. 16/539,569, 9 pages.

* cited by examiner

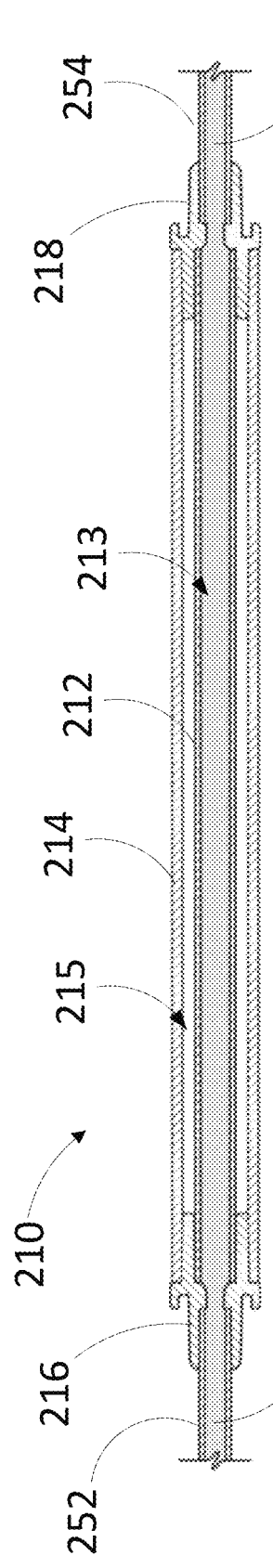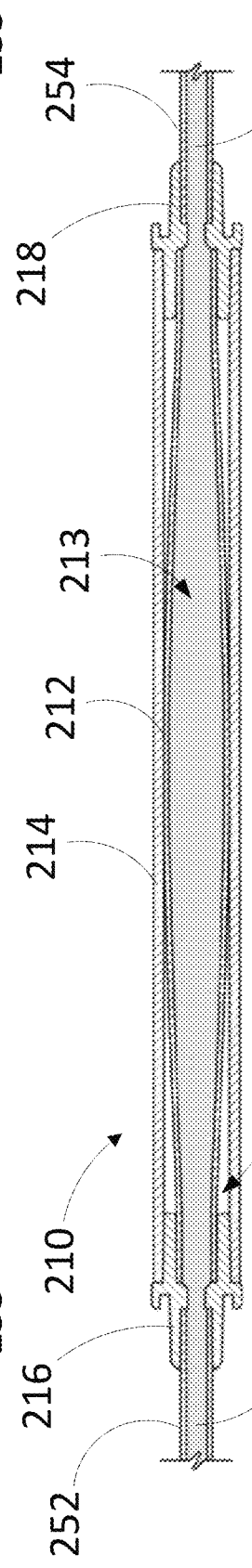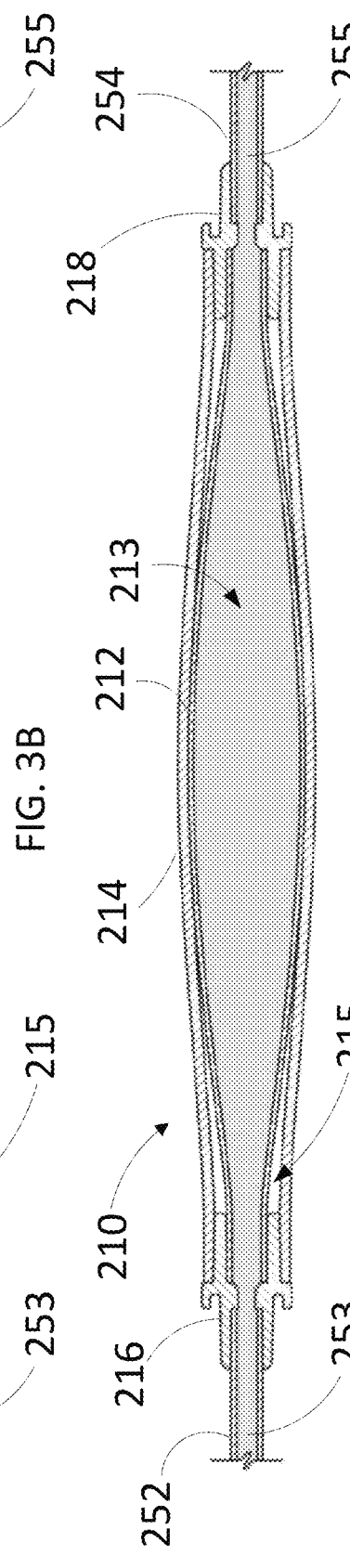
FIG. 3A
FIG. 3B
FIG. 3C

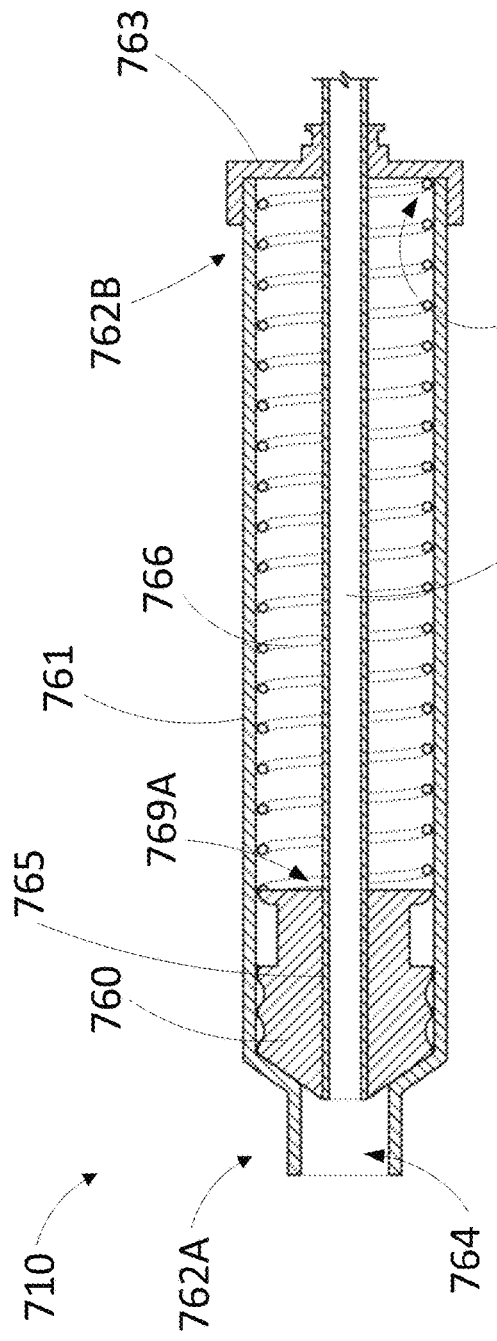
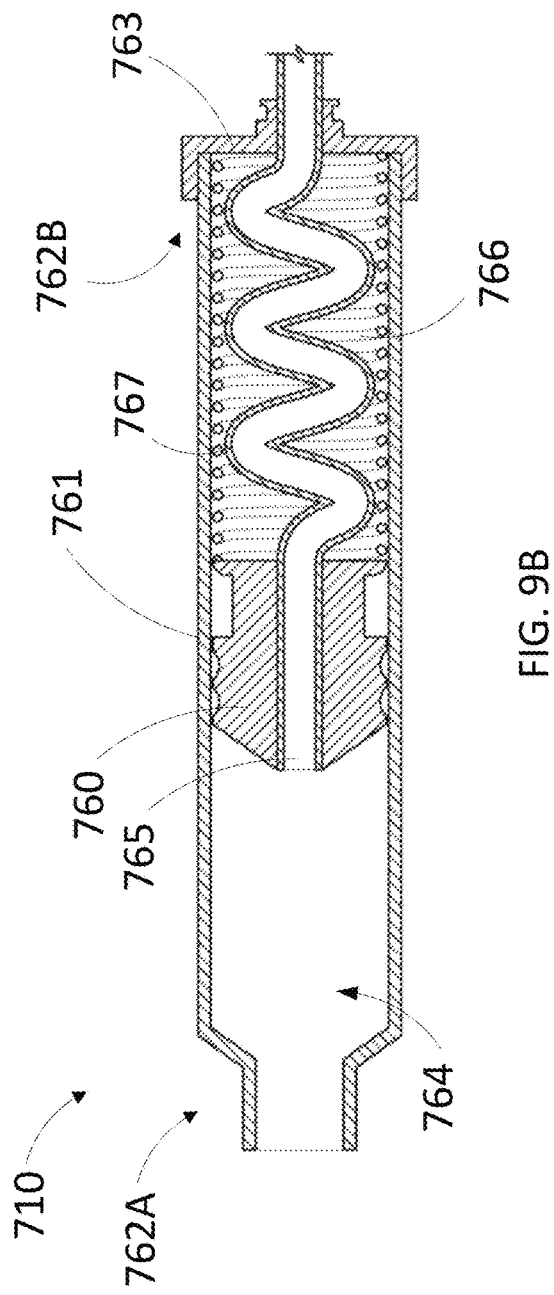
FIG. 9A
FIG. 9B

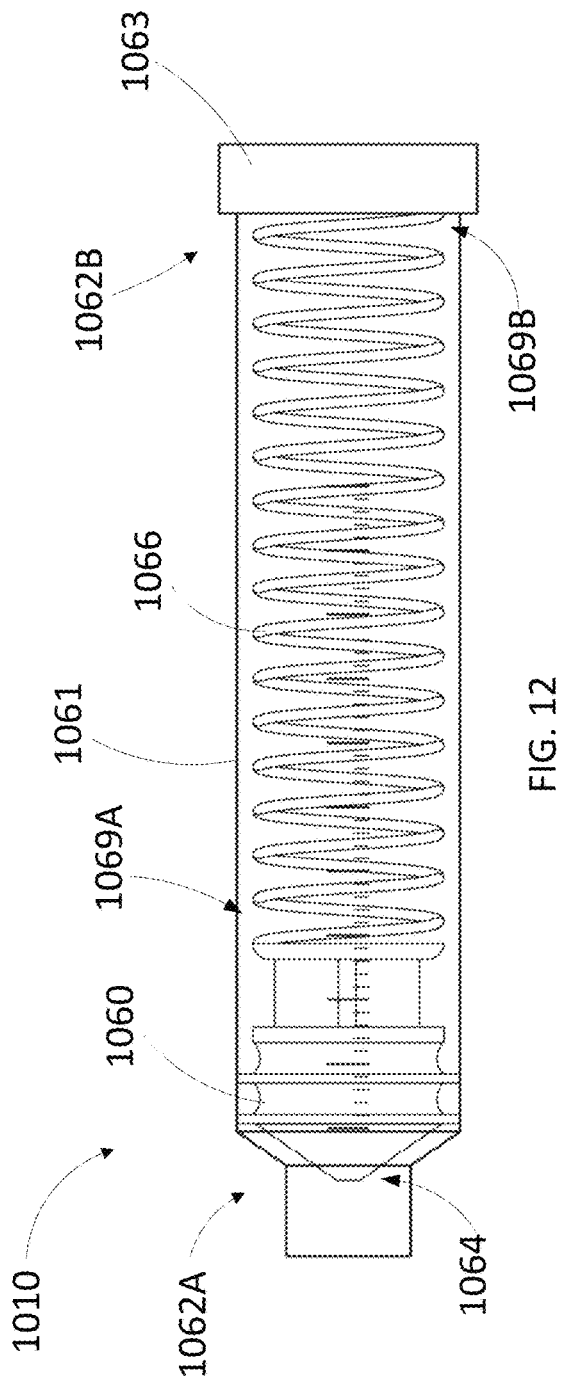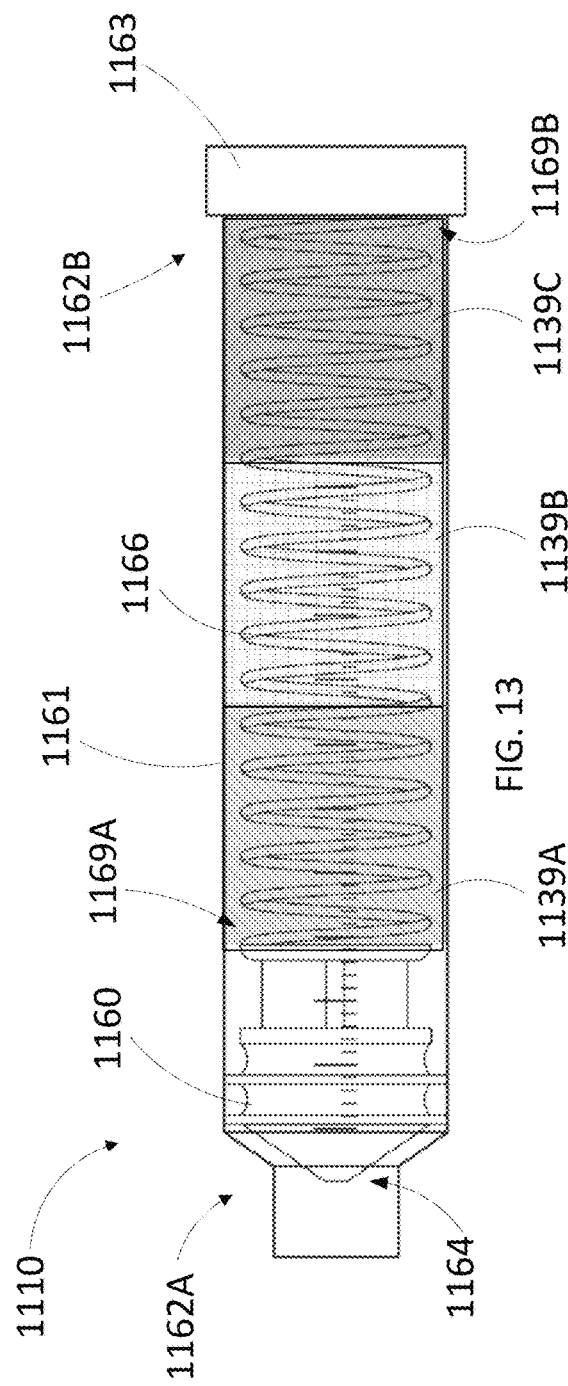

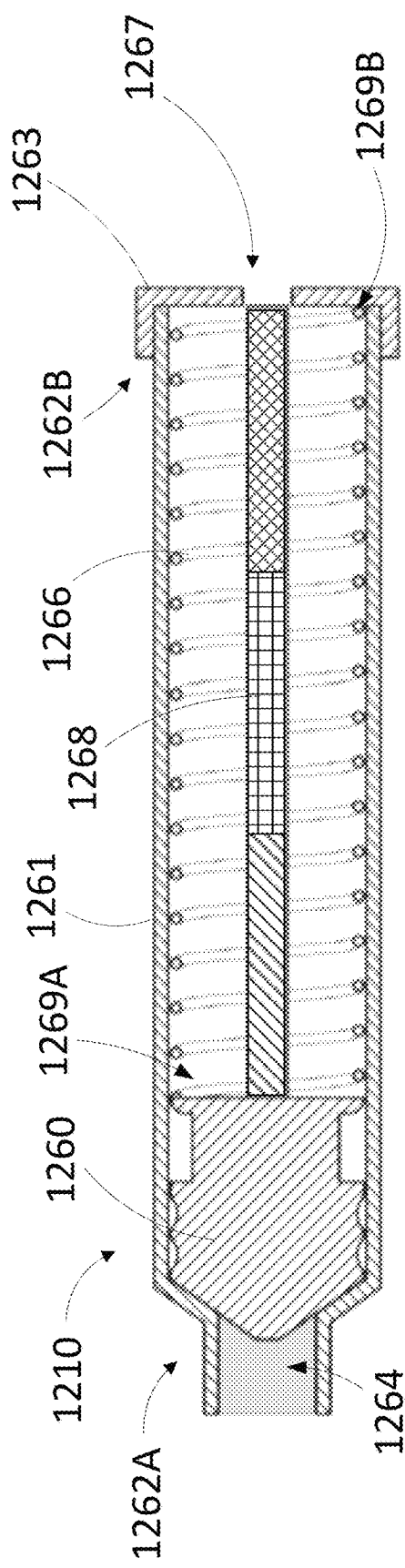
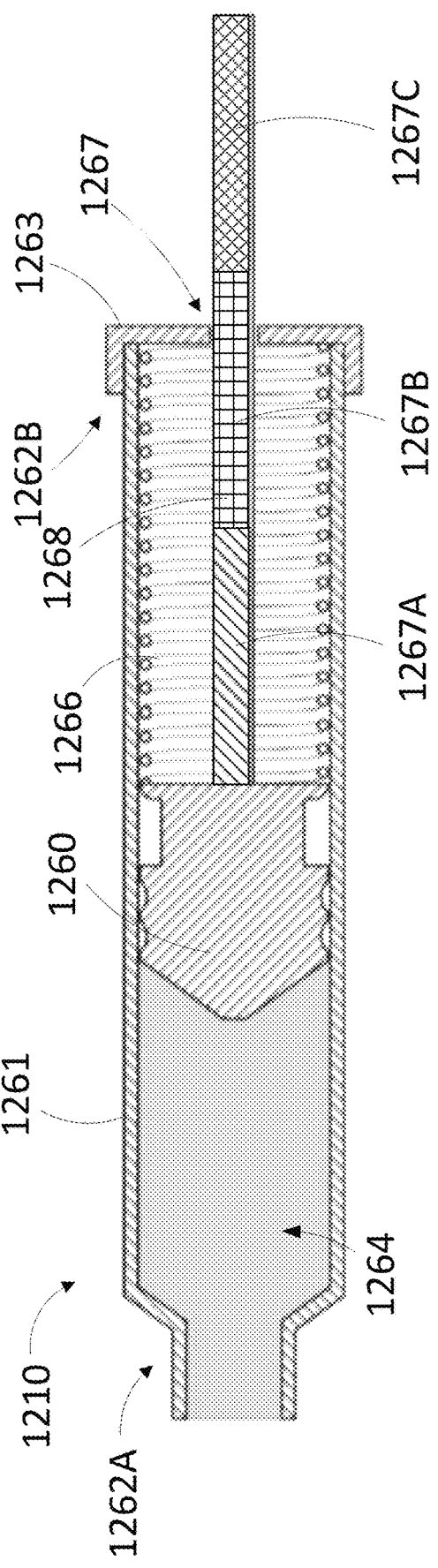
FIG. 14A
FIG. 14B

SYSTEMS, APPARATUS, AND METHODS FOR REDUCING FLUID PRESSURE IN A FLUID LINE

CROSS-REFERENCE TO RELATED APPLICATIONS

This application is a Continuation of U.S. patent application Ser. No. 16/539,569, now U.S. Pat. No. 10,871,788, filed Aug. 13, 2019, which claims priority to and the benefit of U.S. Provisional Patent Application No. 62/718,139, filed Aug. 13, 2018, entitled "Systems, Apparatus, and Methods for Reducing Fluid Pressure in a Fluid Line," the entire contents of which are incorporated by reference herein for all purposes.

BACKGROUND

Embodiments described herein relate to systems, apparatus, and methods for reducing fluid pressure in a fluid line.

Rapid fluid administration can be essential to the survival of patients suffering from shock, which is a life-threatening condition that can result from a variety of causes including bacterial sepsis, hemorrhage, trauma, severe dehydration, and anaphylaxis. The American Heart Association's Pediatric Advanced Life Support (PALS) guidelines, the American College of Critical Care Medicine, and the Surviving Sepsis Campaign guidelines for adults recommend rapid fluid resuscitation as a key element of the initial therapeutic response to shock. For example, PALS recommends the infusion of 20 milliliters of fluid per kilogram of body weight during the first five minutes of the initial therapeutic response and up to 60 milliliters per kilogram of body weight during the first fifteen minutes of the initial therapeutic response.

Common methods for achieving vascular access for fluid delivery to a patient include peripheral venous catheters, central venous catheters, and intraosseous catheters. Each of these catheters include access lumens having small diameters, and thus fluid flow through the catheters is often restricted compared to tubing used to fluidically couple the catheters to a source of fluid. Healthcare providers use various methods and systems to deliver fluid (e.g., intravenous fluids such as saline, blood products, or medicine) rapidly from a reservoir, including gravity-based systems, infusion pumps, pressure bags applied to the fluid reservoir, hand-operated syringes, and/or mechanical rapid-infusion systems. Some of these methods and systems deliver fluid via a near-constant pressure profile, while others deliver fluid via a pulsatile pressure profile.

For example, a hand-operated syringe may deliver fluid (e.g., intravenous fluid such as saline or blood products) via a pulsatile pressure profile, first infusing the entire fluid volume of the syringe through a catheter and then not delivering fluid through the catheter while the syringe is refilled. Hand-operated syringes, however, have benefits over other rapid infusion systems and methods. For example, hand-operated syringes can be used to generate relatively high instantaneous flow rates and fluid pressures. Furthermore, the user can tactilely feel changes in flow resistance (e.g., of fluid flow through a downstream catheter partially disposed within the user's vascular system). A change in tactile feel may indicate a variety of problems, such as infiltration of the catheter, a loose connection in the tubing, and/or other issues that may require addressing. Thus, improved tactile feel for a clinician operating a rapid infusion system may decrease large infiltrations compared to a rapid infusion system that is not closely monitored or provides reduced tactile feedback. A drawback of hand-operated syringes, however, is that all of the fluid flow from the syringe must occur during a compression stroke of the syringe, with no flow occurring from the syringe during a refill period of the syringe. Thus, relatively high user input forces (e.g., the force required to push a plunger of a syringe to deliver the fluid volume) are required to infuse fluid through catheters with small diameter lumens.

Furthermore, when blood and blood products are rapidly infused, a key consideration is how much hemolysis, or destruction of red blood cells, occurs during transfusion. Lysing of red blood cells can occur when high fluid shear force is present on the cells. Lysed red blood cells can no longer carry oxygen to tissue, and the damaged cells also release hemoglobin into the plasma present in the blood, which must be filtered out by the patient's liver. While some hemolysis occurs naturally in the blood stream, elevated levels of hemolysis can have negative clinical consequences.

Therefore, there is a need for systems, apparatus, and methods that can improve the average flow rate of fluid delivered to a patient, particularly when the source of pressurized fluid has a pulsatile pressure profile. Furthermore, there is a need for systems, apparatus, and methods that reduce the user input force required to deliver fluid to a patient while maintaining tactile feel indicative of unwanted downstream flow resistance. Additionally, there is a need for systems, apparatus, and methods that reduce both the peak pressure and instantaneous flow rate present in a tubing system to lower shear forces on red blood cells being transfused by the tubing system and reduce hemolysis present in transfused blood.

SUMMARY

In some embodiments, an apparatus includes a tube portion, a source of pressurized fluid, and a fluid pressure regulating device. The tube portion can have a first end, a second end, and define a lumen extending from the first end to the second end. The second end can be configured to be coupled to a patient access component such that fluid can be delivered from the lumen of the tube portion to a patient via the patient access component. The source of pressurized fluid can be coupled to the first end of the tube portion and can be configured to deliver fluid to the lumen of the tube portion at a source pressure. The source of pressurized fluid can include a fluid receptacle and a one-way valve configured such that fluid can flow from the fluid receptacle, through the one-way valve, and into the lumen of the tube portion and fluid is prevented from flowing from the lumen of the tube portion into the fluid receptacle of the source of pressurized fluid. The fluid pressure regulating device can include an expandable reservoir and can be coupled to the tube portion such that the expandable reservoir is in fluidic communication with the tube portion. The expandable reservoir can be configured to expand from a first configuration having a first volume to a second configuration having a second volume greater than the first volume when a pressure of fluid within the expandable reservoir increases. The expandable reservoir can be resiliently biased toward the first configuration. The fluid pressure regulating device can be configured such that, when fluid is delivered from the fluid receptacle of the source of pressurized fluid to the lumen of the tube portion at the source pressure, the expandable reservoir of the fluid pressure regulating device can receive fluid such that the expandable reservoir of the fluid pressure regulating device expands from the first configuration to the second configuration and fluid is delivered from the lumen of the tube portion to the patient via the patient access component.

BRIEF DESCRIPTION OF THE DRAWINGS

FIG. 3A is a cross-sectional illustration of a fluid pressure regulating device of the system of FIG. 2 in a first configuration.

FIG. 3B is a cross-sectional illustration of the fluid pressure regulating device of the system of FIG. 2 in a second configuration.

FIG. 3C is a cross-sectional illustration of the fluid pressure regulating device of the system of FIG. 2 in a third configuration.

FIG. 9A is a cross-sectional illustration of a fluid pressure regulating device of the system of FIG. 8 in a first configuration.

FIG. 9B is a cross-sectional illustration of the fluid pressure regulating device of the system of FIG. 8 in a second configuration.

FIG. 12 is a side view of a fluid pressure regulating device, according to an embodiment.

FIG. 13 is a side view of a fluid pressure regulating device, according to an embodiment.

FIG. 14A is a side view of a fluid pressure regulating device in a first configuration, according to an embodiment.

FIG. 14B is a side view of the fluid pressure regulating device in a second configuration.

DETAILED DESCRIPTION

Figure 1:
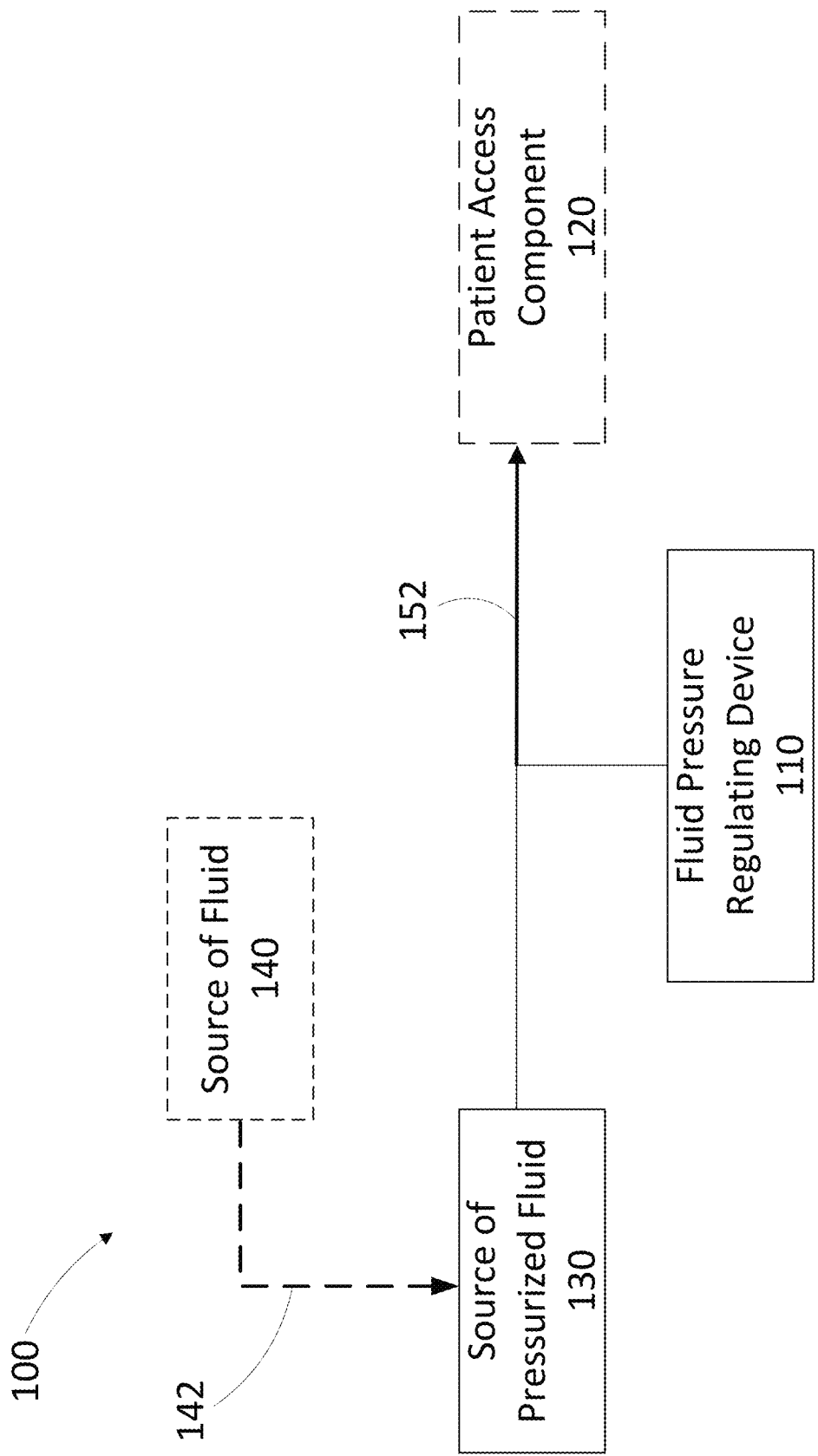
FIG. 1 is a schematic illustration of a system, according to an embodiment.

In some embodiments, an apparatus includes a tube portion, a source of pressurized fluid, and a fluid pressure regulating device. The tube portion can have a first end, a second end, and define a lumen extending from the first end to the second end. The second end can be configured to be coupled to a patient access component such that fluid can be delivered from the lumen of the tube portion to a patient via the patient access component. The source of pressurized fluid can be coupled to the first end of the tube portion and can be configured to deliver fluid to the lumen of the tube portion at a source pressure. The source of pressurized fluid can include a fluid receptacle and a one-way valve configured such that fluid can flow from the fluid receptacle, through the one-way valve, and into the lumen of the tube portion and fluid is prevented from flowing from the lumen of the tube portion into the fluid receptacle of the source of pressurized fluid. The fluid pressure regulating device can include an expandable reservoir and can be coupled to the tube portion such that the expandable reservoir is in fluidic communication with the tube portion. The expandable reservoir can be configured to expand from a first configuration having a first volume to a second configuration having a second volume greater than the first volume when a pressure of fluid within the expandable reservoir increases. The expandable reservoir can be resiliently biased toward the first configuration. The fluid pressure regulating device configured such that, when fluid is delivered from the fluid receptacle of the source of pressurized fluid to the lumen of the tube portion at the source pressure, the expandable reservoir of the fluid pressure regulating device can receive fluid such that the expandable reservoir of the fluid pressure regulating device expands from the first configuration to the second configuration and fluid is delivered from the lumen of the tube portion to the patient via the patient access component.

In some embodiments, an apparatus includes an outer tube and an inner tube. The outer tube can have a first end and a second end and can define a lumen. The inner tube can have a first end and a second end and can define a reservoir having a first volume. The inner tube can be disposed within the lumen of the outer tube. The first end of the inner tube can be coupled to the first end of the outer tube via a first end connector. The second end of the inner tube can be coupled to the second end of the outer tube via a second end connector. The first end connector can be configured to be coupled to a first tube portion such that a lumen of the first tube portion is in fluidic communication with the reservoir of the inner tube. The second end connector can be configured to be coupled to a second tube portion such that a lumen of the second tube portion is in fluidic communication with the reservoir of the inner tube. A sidewall portion of the inner tube can be sufficiently compliant such that the inner tube is configured to expand laterally relative to a central axis of the inner tube (e.g., radially) when a pressure level of a fluid within the reservoir increases such that the reservoir has a second volume greater than the first volume. The sidewall portion can be resiliently biased toward the first volume such that the inner tube is configured to apply a force to the fluid within the reservoir to expel the fluid from the reservoir as the pressure level of the fluid within the reservoir decreases.

In some embodiments, an apparatus includes a housing, a spring member, and a seal member. The housing can define an interior and can have a first end and a second end. The first end of the housing can be configured to be fluidically coupled to a tube portion. The spring member can be disposed within the interior of the housing and can have a first end and a second end. The second end of the spring member can be coupled to the second end of the housing. The spring member can be resiliently biased toward an expanded configuration. The seal member can be disposed in the interior of the housing and coupled to the first end of the spring member. The seal member and the housing can collectively define a reservoir having a first volume. The seal member can be configured to translate within the interior of the housing such that, when the first end of the housing is fluidically coupled to the tube portion such that the tube portion is in fluidic communication with the reservoir and when a fluid pressure of a fluid in the tube portion and the reservoir increases, the fluid applies a force to the seal member such that the seal member translates toward the second end of the housing and the spring member transitions from the expanded position to a compressed position such that the volume of the reservoir increases from the first volume to a second volume greater than the first volume as fluid is received into the reservoir.

In some embodiments, an apparatus can include a housing and a seal member. The housing can define an interior and can have a first end and a second end. The first end of the housing can be configured to be fluidically coupled to a tube portion. The seal member can be disposed in the interior of the housing and can have a first side and a second side. The first side of the seal member and the housing can collectively define a first reservoir having a first volume. The second side of the seal member and the housing can collectively define a second reservoir having a second volume. The second reservoir is fluidically isolated from the first reservoir. The seal member can be configured to translate within the interior of the housing such that, when the first end of the housing is fluidically coupled to the tube portion such that a lumen of the tube portion is in fluid communication with the reservoir and when a fluid pressure of a fluid in the lumen of the tube portion and the reservoir increases, the fluid can apply a force to the seal member such that the seal member translates toward the second end of the housing and compresses a gas disposed within the second reservoir such that the volume of the first reservoir increases as fluid is received into the first reservoir from the lumen of the tube portion.

In some embodiments, a method includes expelling fluid from a fluid pressure source to a tube portion at a source pressure such that fluid is delivered to a patient via the tube portion and fluid is delivered into a reservoir of a fluid pressure regulating device. The fluid pressure regulating device can be coupled to the tube portion such that the reservoir of the fluid pressure regulating device is in fluidic communication with a lumen of the tube portion. The fluid delivered into the reservoir can cause a volume of the reservoir to increase. The method can further include discontinuing the expelling of fluid from the fluid pressure source to the tube portion and allowing the fluid pressure regulating device to deliver fluid from the reservoir of the fluid pressure regulating device to the patient via the tube portion.

The average fluid flow rate through a given lumen (e.g., a catheter lumen) is approximately proportional to the average fluid pressure. Syringe-based methods of infusion have the benefit of being able to generate relatively high instantaneous fluid pressures, generated by clinician input force, but since their pressure profiles are pulsatile in nature, flow through the catheter only occurs during a fraction of the overall infusion time. To achieve the same flow rate as an infusion method having a constant or near-constant pressure profile, a clinician operating an infusion method with a pulsatile profile must input higher instantaneous input forces to make up for the periods in which the syringe is being refilled and not infusing through the catheter. For hand-operated syringes, the instantaneous fluid pressure in the syringe is proportional to the instantaneous force applied to the syringe plunger.

By including an expandable reservoir in the fluid pathway of an infusion tubing set, a pulsatile pressure profile may be smoothed into a more-constant pressure profile, requiring lower instantaneous input force from the user to achieve the same average flow rate as a system with no expandable reservoir. For an infusion method with a pulsatile pressure profile without an expandable reservoir, all of the fluid must pass through the catheter during the high-pressure period of the cycle. With an expandable reservoir in-line with the fluid pathway, a portion of the fluid will pass through the catheter and a portion will be stored in the reservoir, expanding the reservoir, during the compression of the syringe plunger. After the compression period of the cycle ends, the fluid that has accumulated in the reservoir is expelled through the catheter, and is prevented from returning to the syringe by a one-way valve disposed between the expandable reservoir and the syringe. Flow can continue while the syringe plunger is retracted, and the syringe can be refilled from a fluid source. Thus, fluid can be expelled through the catheter during the entire syringe cycle.

Figure 4:
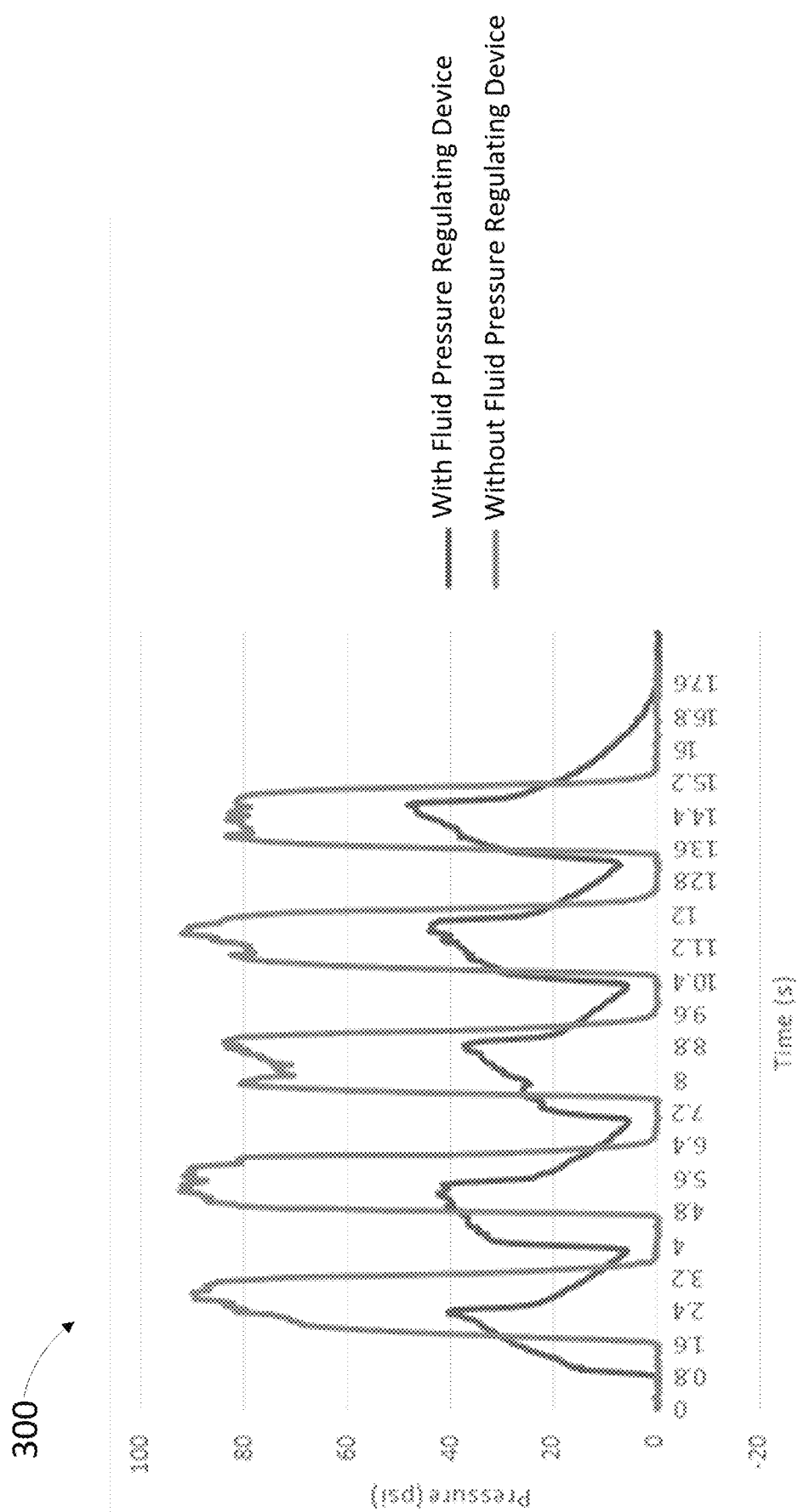
FIG. 4 is a graph showing a comparison between a system including a fluid pressure regulating device and a system not including a fluid pressure regulating device operated such that fluids are delivered from each system at the same average infusion speed, according to an embodiment.

The overall effect of including an expandable reservoir in-line with the fluid pathway for a hand-operated syringe is to decrease the amount of input force required by the user to deliver fluid through a particular catheter size at a particular speed. For example, FIG. 4 shows a graph 300 demonstrating an example comparison of two pressure profiles having the same average infusion rate, i.e. the same total volume of fluid delivered in the same total time. (The fluid rate is proportional to pressure.) One pressure profile reflects the pressure level of fluid near a patient access component (e.g., a catheter partially disposed in a patient) in a system including an expandable reservoir, the other pressure profile reflects the pressure level of fluid near a patient access component (e.g., a catheter partially disposed in a patient) in a system not including an expandable reservoir. FIG. 4 shows that, when using an expandable reservoir, the user was able to deliver fluid with the same average infusion rate while applying significantly less pressure to a hand-operated syringe used as the source of pressurized fluid in the system.

Figure 5:
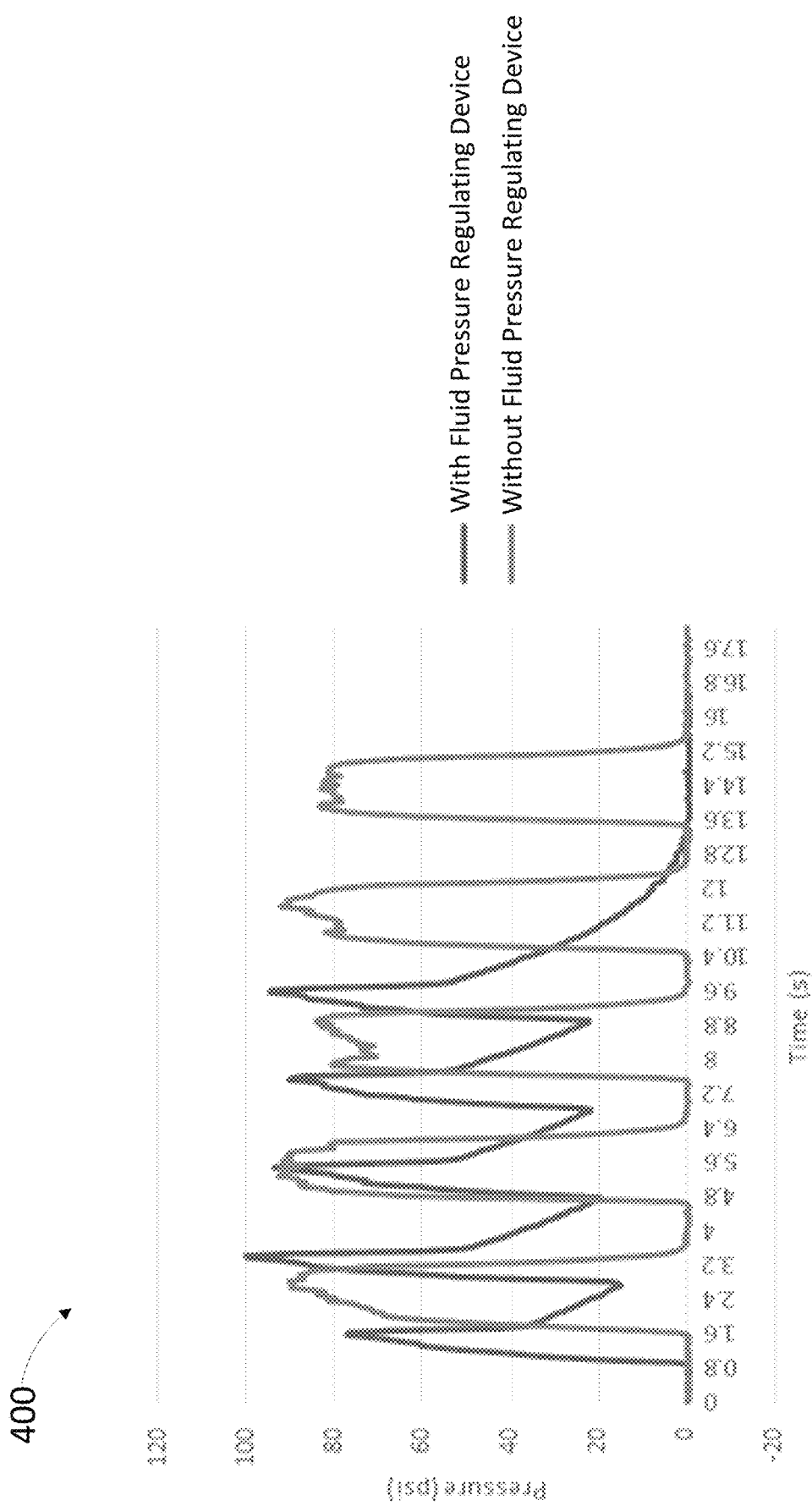
FIG. 5 is a graph showing a comparison between a system including a fluid pressure regulating device and a system not including a fluid pressure regulating device operated such that fluids are delivered to a tube portion of each system at the same source pressure, according to an embodiment.

Furthermore, if a user applies the same amount of force to a hand-operated syringe with an expandable reservoir as the user applies to a syringe with no expandable reservoir, the effect is an increase in average infusion rate. For example, FIG. 5 shows a graph 400 demonstrating an example comparison of two pressure profiles reflecting about the same input force to a hand-operated syringe (e.g., via applying force to a plunger of the syringe), one pressure profile reflecting the pressure level of fluid near a patient access component (e.g., a catheter partially disposed in a patient) in a system including an expandable reservoir, the other pressure profile reflecting the pressure level of fluid near a patient access component (e.g., a catheter partially disposed in a patient) in a system not including an expandable reservoir. FIG. 5 shows that, when using an expandable reservoir, the user was able to deliver five cycles of fluid volume from a syringe (i.e. five full strokes of the syringe) in a shorter overall time than when the user delivered five cycles of fluid volume from a syringe in a system without an expandable reservoir.

FIG. 1 is a schematic illustration of a system 100. The system 100 includes a fluid pressure regulating device 110, a patient access component 120, and a source of pressurized fluid 130. The source of pressurized fluid 130 can be fluidically coupled to the patient access component 120 and the fluid pressure regulating device 110. As shown in FIG. 1, the source of pressurized fluid 130 can be coupled to the patient access component 120 via a tube portion 152. The tube portion 152 can have a first end, a second end, and define a lumen. The source of pressurized fluid 130 can be coupled to the fluid pressure regulating device 110 via any suitable fluid coupling component such as a second tube portion and/or a tubing connector. The fluid pressure regulating device 110 can be fluidically coupled to the patient access component 120 via the tube portion 152. The source of pressurized fluid 130 can optionally be coupled to a source of fluid 140 (e.g., a fluid bag) via a source tube 142 such that the source of fluid 140 can provide fluid (e.g., intravenous fluid, blood, or blood products) to the source of pressurized fluid 130 such that the source of pressurized fluid can deliver pressurized fluid to the patient access component 120 and/or the fluid pressure regulating device 110.

The fluid pressure regulating device 110 can include an expandable reservoir and can be coupled to the source of pressurized fluid 130 and the tube portion 152 such that the expandable reservoir of the fluid pressure regulating device 110 can be in fluidic communication with the source of pressurized fluid 130 and the tube portion 152. The expandable reservoir can be configured to expand such that a volume of the expandable reservoir increases as the pressure of fluid within the expandable reservoir increases. For example, the expandable reservoir can be configured to expand from a first configuration having a first volume to a second configuration having a second volume greater than the first volume when a pressure of fluid within the expandable reservoir increases. The expandable reservoir can be resiliently biased toward a configuration corresponding to a smaller volume. For example, the expandable reservoir can be resiliently biased toward the first configuration. Thus, the expandable reservoir can be configured to apply a force to fluid within the reservoir such that the expandable reservoir can expel fluid from the expandable reservoir when the force applied by the fluid within the expandable reservoir on the expandable reservoir due to fluid pressure is less than the force applied by the expandable reservoir on the fluid due to the bias of the expandable reservoir toward a smaller volume configuration.

The source of pressurized fluid 130 can be any suitable device configured to provide fluid to the tube portion 152. In some embodiments, the source of pressurized fluid 130 is configured to draw fluid from the source of fluid 140 via the source tube 142 and to expel fluid such that fluid is delivered to the tube portion 152. In some embodiments, the source of pressurized fluid 130 can alternate between an expulsion state in which the source of pressurized fluid 130 expels fluid from the reservoir (also referred to herein as a "fluid receptacle") of the source of pressurized fluid 130 into the lumen of the tube portion 152 and a drawing state in which the source of pressurized fluid 130 draws fluid from the fluid source 140 into the reservoir of the source of pressurized fluid 130. In some embodiments, the source of pressurized fluid can include a reciprocating actuator configured to deliver a discrete volume of fluid from a reservoir of the source of pressurized fluid 130 with each cycle of the reciprocating actuator. Each cycle may include a drawing portion in which fluid is drawn into the reservoir of the source or pressurized fluid 130 from the source of fluid 140 and a delivery portion in which fluid is expelled from the reservoir of the source of pressurized fluid 130 to the tube portion 152.

In some embodiments, the source of pressurized fluid 130 can include a syringe and a dual check valve assembly. The syringe can include a syringe barrel, a seal member, and a plunger. The syringe barrel and the plunger can collectively define a reservoir of the source of pressurized fluid. The dual check valve assembly can include a first one-way valve and a second one-way valve. The syringe and dual check valve assembly can be configured such that, when the plunger is being pushed distally (e.g., toward the tube portion 152) relative to the syringe barrel such that the seal member is translated distally, the source of pressurized fluid 130 can deliver fluid through the first one-way valve of the dual check valve assembly such that fluid is delivered to the patient access component 120 via the tube portion 152 and to the expandable reservoir of the fluid pressure regulating device 110. The syringe and dual check valve assembly can also be configured such that, when the plunger is being translated proximally (e.g., away from the tube portion 152) relative to the syringe barrel such that the seal member is translated proximally, the first one-way valve can fluidically isolate the reservoir of the syringe from the lumen of the tube portion 152 and fluid can be drawn from the fluid source 140, through the second one-way valve, and into the reservoir of the syringe. In some embodiments, the syringe can be manually-operated such that the plunger of the syringe is translated (e.g., pushed and pulled) directly, manually by a user (e.g., a healthcare provider). In some embodiments, the source of pressurized fluid 130 can include a delivery device configured to be actuated (e.g., manually or automatically) to control the translation of the plunger of the syringe. In some embodiments, rather than including a separate source of fluid 140, the source of pressurized fluid can include a squeezable fluid bag configured to be squeezed by a user to expel fluid from the bag into the tube portion 152.

The patient access component 120 can be any suitable component configured to be fluidically coupled to the tube portion 152 to deliver fluid from the tube portion 152 into a patient. For example, the patient access component 120 can include a catheter, a needle, and/or a port. In some embodiments, the patient access component 120 can include a peripheral venous catheter, a central venous catheter, or an intraosseous catheter. In some embodiments, the patient access component 120 can include at least a portion configured to be at least partially disposed within a patient and having a lumen with a smaller diameter than the diameter of the lumen of the tube portion 152.

Although only the tube portion 152 is shown in FIG. 1 as being included in the system 100, the system 100 can include any suitable number of tube portions and/or fluid connectors. For example, in some embodiments, the tube portion 152 can be a first tube portion and a second tube portion can couple the tube portion 152 to the source of pressurized fluid 130 and/or the fluid pressure regulating device 110. The second tube portion can have a first end, a second end, and define a lumen. In some embodiments, the fluid pressure regulating device 110 can define an inlet and an outlet such that fluid can travel into the expandable reservoir of the fluid pressure regulating device 110 via the inlet and fluid can travel out of the expandable reservoir of the fluid pressure regulating device 110 via the outlet. The first end of the first tube portion 152 can be coupled to the patient access component 120 and the second end of the first tube portion 152 can be coupled to the outlet of the fluid pressure regulating device 110. The first end of the second tube portion can be coupled to the inlet of the fluid pressure regulating device 110 and the second end of the second tube portion can be coupled to the source of pressurized fluid 130. Thus, fluid can travel from the reservoir of the source of pressurized fluid 130, through the second tube portion, through the expandable reservoir of the fluid pressure regulating device 110, through the first tube portion 152, through the patient access component 120, and into the patient. In some embodiments, the fluid pressure regulating device 110 can be fluidically coupled to the first tube portion 152 via a fluid connector defining an interior. For example, the fluid connector can be coupled to the second end of the tube portion 152 and the patient access component 120 can be coupled to the first end of the tube portion 152. In some variations, the fluid connector can be coupled to the source of pressurized fluid 130 such that the reservoir of the source of pressurized fluid 130 and the expandable reservoir of the fluid pressure regulating device 110 can be in fluidic communication via the interior of the fluid connector. In some variations, the fluid connector can be coupled to the source of pressurized fluid 130 via a second tube portion.

In some embodiments, the expandable reservoir of the fluid pressure regulating device 110 can be in selective fluidic communication with the source of pressurized fluid 130 and in open fluid communication with the tube portion 152. For example, the source of pressurized fluid 130 can include a one-way valve disposed between the reservoir of the source of pressurized fluid 130 and the fluid pressure regulating device 110 such that the expandable reservoir of the fluid pressure regulating device 110 is in selective fluid communication with the reservoir of the source of pressurized fluid. The fluid path between the expandable reservoir of the fluid pressure regulating device 110 and the tube portion 152 can be open such that fluid can flow freely between the expandable reservoir and the lumen of the tube portion 152. Thus, the pressure level of the fluid in the lumen of the tube portion 152 can be about equal to the pressure level of the fluid in the expandable reservoir due to the lumen of the tube portion 152 and the expandable reservoir being in fluid communication.

The expandable reservoir can be resiliently biased towards its lower volume configuration with any suitable spring rate (e.g. constant rate) or spring rate profile (e.g. spring rate that varies with displacement distance). In some embodiments, the spring rate or spring rate profile can be selected depending, at least in part, on the diameter of the lumen of the tube portion 152, the diameter of a fluid access lumen of the patient access component 120, and/or the intended fluid flow rate through the patient access component 120. In some embodiments, the spring rate or spring rate profile can be selected depending, at least in part, on the source pressure of the fluid leaving the source of pressurized fluid 130, the volume of fluid expelled with each expulsion cycle from the source of pressurized fluid 130, and/or the frequency of expulsions of fluid from the source of pressurized fluid 130. In some embodiments, the spring rate or spring rate profile can be selected depending, at least in part, on the desired input force required to deliver fluid from the source of pressurized fluid 130 (e.g., force required to translate a syringe plunger to deliver the fluid contents of the syringe). In some embodiments, the spring rate or spring rate profile can be selected depending, at least in part, on maintaining the reliability of tactile feel so the user can detect occlusions in the fluid path between the source of pressurized fluid 130 and the patient and on preventing the fluid pressure regulating device 110 from causing a false sense of occlusion.

In some embodiments, the spring rate or spring rate profile can be selected based on any suitable combination of factors. For example, an expandable reservoir with a sufficiently low spring rate will accumulate more fluid than can be expelled through the patient access component 120 during a drawing or refill cycle of a syringe of the source of pressurized fluid 130. Thus, the expandable reservoir will accumulate progressively more fluid with each syringe cycle, diminishing the force-reducing effect and potentially causing the expandable reservoir to rupture. Alternatively, an expandable reservoir with a sufficiently high spring rate will accumulate less fluid than can be ejected through the patient access component 120 during the syringe refill or drawing cycle of the source of pressurized fluid 130, resulting in less of a force-reducing effect than would be possible with a lower spring rate. In some embodiments, the smaller the patient access lumen of the patient access component 120, the higher pressure required to deliver fluid through the patient access component 120 during, for example, a syringe refill or drawing cycle of the source of pressurized fluid 130, and thus a higher spring rate may be needed. In some embodiments, the larger the input force used (e.g., the force applied to a plunger of a syringe of the source of pressurized fluid 130), the higher expandable reservoir spring rate needed because more fluid will accumulate in the expandable reservoir during the compression cycle of the source of pressurized fluid 130 than if the input force were smaller.

In some embodiments, the source of pressurized fluid 130 can have a refill time of 1.2 seconds and the fluid pressure regulating device 110 can have a spring rate of about 6 psi/ml and the tube portion 152 and/or the patient access component 120 can include a 20 gauge catheter such that the refill time of the source of pressurized fluid 130 is the same or similar to the time taken for the expandable reservoir to return to its first, lower volume configuration. In some embodiments, the source of pressurized fluid 130 can have a refill time of 0.25 seconds and the fluid pressure regulating device 110 can have a spring rate of about 6 psi/ml and the tube portion 152 and/or the patient access component 120 can include a 16 gauge catheter such that the refill time of the source of pressurized fluid 130 is the same or similar to the time taken for the expandable reservoir to return to its first, lower volume configuration.

The "spring rate" as used herein is a ratio of the pressure of fluid disposed within the expandable reservoir (e.g., in pounds per square inch) to the change in volume of fluid (e.g., in milliliters) within the expandable reservoir. The spring rate can be determined (e.g., measured) by closing off an outlet of the fluid pressure regulating device 110, coupling a pressure measuring device (e.g., a pressure gauge) in fluid communication with the expandable reservoir of the fluid pressure regulating device 110 (e.g., at the outlet), and adding fluid to the expandable reservoir of the fluid pressure regulating device 110 while monitoring the change in pressure of the fluid within the expandable reservoir with the pressure measuring device. Fluid can be added to the interior of the fluid pressure regulating device 110 in 1 milliliter increments and coordinates representing the pressure and volume within the expandable reservoir at various incremental volumes (e.g., 7 ml, 8 ml, 9 ml) can be plotted. The spring rate can be equal to a slope of a curve including the plotted pressure versus volume coordinates. Thus, a more rigid expandable reservoir can have a higher spring rate than a more compliant expandable reservoir since the volume of the more compliant expandable reservoir can increase more compared to the more rigid expandable reservoir before a given pressure is reached.

Figure 17:
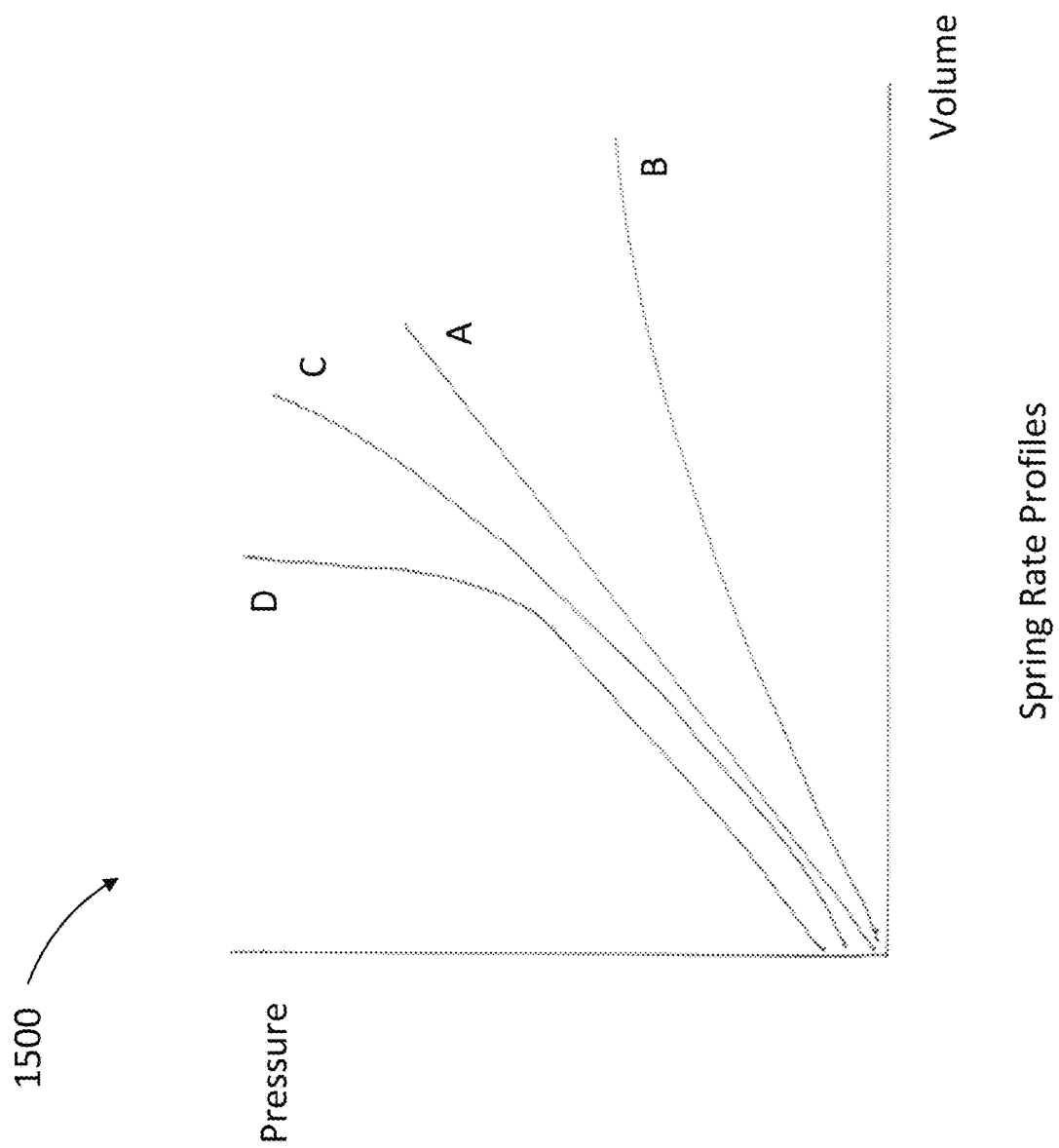
FIG. 17 is a graph illustrating various possible fluid pressure regulating device spring rate profiles, according to an embodiment.

As shown in FIG. 17, which is a graph illustrating various spring rate profiles, the expandable reservoir can have a variety of spring rate profiles. In some embodiments, the expandable reservoir can have a linear spring rate profile, i.e. a constant spring rate, represented as curve A. Such an expandable reservoir would have the same spring rate throughout the expulsion cycle, regardless of the volume of the expandable reservoir. In some embodiments, the expandable reservoir can have a regressive spring rate, represented as curve B. Such an expandable reservoir would have a spring rate that decreases as the volume of the expandable reservoir increases. A downside to expandable reservoirs with regressive spring rates, however, is that, as the volume of the expandable reservoir increases, the user may lose tactile feel and not be able to identify obstructions or problems with the fluid path. In some embodiments, the expandable reservoir can have a progressive spring rate, represented as curve C. For example, a progressive spring rate can be achieved by including a compliant outer tube against which an inner tube can expand such that both the outer tube and the inner tube continue expanding together. As another example, a progressive spring rate can be achieved by including two coil springs arranged in parallel or in series and coupled to a translatable sealing member, the coil springs having different spring rates. An expandable reservoir with a progressive spring rate has the benefit of maintaining tactile feel for the user without distinct transition points in the spring rate profile. Furthermore, an expandable reservoir with a progressive spring rate has the benefit of allowing the use of a wide range of catheter sizes, user input forces, and/or source pressures in conjunction with the expandable reservoir. In some embodiments, the expandable reservoir can have a spring rate profile having a distinct transition point, such as is represented by curve D. For example, a spring rate profile with a distinct transition point can be achieved by including a rigid outer tube against which an inner tube can expand such that further expansion is restrained. A downside to a spring rate profile with a distinct transition point is that the user may not be able to distinguish between the transition point of the spring rate profile and an occlusion in the fluid path downstream of the source of pressurized fluid 130.

A spring rate may be defined as the slope of the pressure vs. volume curve of an expandable reservoir at a given point on the curve. In some embodiments, the expandable reservoir of the fluid pressure regulating device 110 is configured to have an average spring rate of between 0.5 and 20 psi/ml. When the patient access component 120 includes a catheter such as a peripheral venous catheter, a central venous catheter, or an intraosseous catheter and the source of pressurized fluid 130 includes a hand-operated syringe, for example, spring rates less than 0.5 psi/ml may generate insufficient pressure to eject accumulated fluid from the expandable reservoir through the patient access component 120 and spring rates greater than 20 psi/mL may not expand sufficiently to provide a force reduction effect that is noticeable (e.g., via tactile feedback) during use. As described above, in some embodiments, the fluid pressure regulating device 110 can have a spring rate of about 6 psi/ml.

In use, the source of pressurized fluid 130 can deliver fluid at a source pressure to the tube portion 152 of the fluid pressure regulating device 110. As a result of being in fluid communication with the tube portion 152, the expandable reservoir of the fluid pressure regulating device 110 can receive fluid such that the expandable reservoir expands in volume. For example, the expandable reservoir can have an initial configuration (e.g., a first configuration), and can expand to a second configuration having a second volume greater than the first volume. While the expandable reservoir is receiving fluid, fluid can be delivered from the lumen of the tube portion 152 to the patient via the patient access component 120. Due to a portion of the fluid from the source of pressurized fluid 130 being diverted to and/or into the fluid pressure regulating device 110, the fluid pressure of the fluid delivered via the patient access component 120 may be lower than the fluid pressure of fluid delivered from a source of pressurized fluid and not partially diverted using a fluid pressure regulating device.

In some embodiments, the source of pressurized fluid 130 can discontinue delivering fluid to the lumen of the tube portion 152. For example, the source of pressurized fluid 130 can discontinue an expelling stroke or expelling portion of an operation cycle such that fluid is no longer expelled through the one-way valve to the tube portion 152, and instead a drawing stroke or drawing portion of an operation cycle can be initiated such that fluid is drawn from the source of fluid 140 into the reservoir of the source of pressurized fluid 130. During the period when the source of pressurized fluid 130 is not delivering fluid to the tube portion 152 and the expandable reservoir has a volume greater than the volume of the expandable reservoir in the initial configuration, the expandable reservoir of the fluid pressure regulating device 110 can expel fluid from the expandable reservoir into the tube portion 152 such that fluid is delivered from the tube portion 152 to the patient via the patient access component via decreasing the size of the expandable reservoir. In some embodiments, the expandable reservoir can continue to expel fluid until the expandable reservoir has decreased to the first configuration of the expandable reservoir. In some embodiments, the expandable reservoir can expel fluid until the source of pressurized fluid 130 starts delivering fluid to the tube portion 152 again, at which time the expandable reservoir may be at a volume greater than the volume corresponding to the first configuration. As the source of pressurized fluid 130 delivers fluid to the tube portion 152, the expandable reservoir can receive fluid such that the expandable reservoir again expands. Thus, as the source of pressurized fluid 130 alternates between an expulsion state and a drawing state, the system 100 can deliver fluid to the patient via the patient access component 120 during both the expulsion state and the drawing state of the source of pressurized fluid 130.

In some embodiments, the fluid pressure regulating device 110 can include an outer tube and an inner tube. The outer tube can have a first end and a second end and can define a lumen. The inner tube can have a first end and a second end and can define an expandable reservoir. The expandable reservoir can have a first volume. The inner tube can be disposed within the lumen of the outer tube. The first end of the inner tube can be coupled to the first end of the outer tube via a first end connector. The second end of the inner tube can be coupled to the second end of the outer tube via a second end connector. The first end connector can be configured to be coupled to a first tube portion such that a lumen of the first tube portion is in fluidic communication with the reservoir of the inner tube. The second end connector can be configured to be coupled to a second tube portion such that a lumen of the second tube portion is in fluidic communication with the reservoir of the inner tube. The inner tube can include a sidewall portion that is sufficiently compliant such that the inner tube is configured to expand laterally relative to a central axis of the inner tube when a pressure level of a fluid within the reservoir increases such that the reservoir has a second volume greater than the first volume. The sidewall portion can be resiliently biased toward the first volume such that the inner tube is configured to apply a force to the fluid within the reservoir to expel the fluid from the reservoir as the pressure level of the fluid within the reservoir decreases.

In some embodiments, the outer tube can have a first outermost diameter and can be expandable such that, when the inner tube is expanded such that an outer surface of the inner tube applies pressure to an inner surface of the outer tube, the outer tube is configured to expand laterally relative to a central axis of the outer tube. The outer tube can be resiliently biased toward the first outermost diameter and, after the inner tube is expanded such that an outer surface of the inner tube applies pressure to an inner surface of the outer tube, the outer tube can apply a force to the outer surface of the inner tube such that the force applied by the inner tube to the fluid within the reservoir includes the force applied by the outer tube to the outer surface of the inner tube. In some embodiments, the second lumen can be partially formed by the sidewall portion of the first lumen.

In some embodiments, the outer tube can be rigid such that, when the inner tube is expanded such that an outer surface of the inner tube applies pressure to an inner surface of the outer tube, the outer tube prevents further lateral expansion of the inner tube.

In some embodiments, the fluid pressure regulating device 110 can include a housing, a spring member, and a seal member. The housing can define an interior and can have a first end and a second end. The first end of the housing can be configured to be fluidically coupled to a tube portion. The spring member can be disposed within the interior of the housing and can have a first end and a second end. The second end of the spring member can be coupled to the second end of the housing. The spring member can be resiliently biased toward an expanded configuration. The seal member can be disposed in the interior of the housing and coupled to the first end of the spring member. The seal member and the housing can collectively define an expandable reservoir having a first volume. The seal member can be configured to translate within the interior of the housing such that, when the first end of the housing is fluidically coupled to the tube portion such that the tube portion is in fluidic communication with the reservoir and when a fluid pressure of a fluid in the tube portion and the reservoir increases, the fluid applies a force to the seal member such that the seal member translates toward the second end of the housing and the spring member transitions from the expanded position to a compressed position such that the volume of the reservoir increases from the first volume to a second volume greater than the first volume as fluid is received into the reservoir.

In some embodiments, when the fluid pressure of the fluid in the tube portion and the reservoir decreases, the spring member can transition from the retracted position to the expanded position such that the volume of the reservoir decreases as fluid is expelled from the reservoir into the tube portion. In some embodiments, the housing can define an opening in the second end and the seal member includes an extending member extending away from the first end of the housing, the extending member configured to slidably extend through the opening in the second end of the housing and project a first distance from the second end of the housing when the volume of the reservoir is the first volume and to project a second distance from the second end of the housing when the reservoir is a second volume greater than the first volume. In some embodiments, the extending member can include at least one indicator corresponding to a volume of the reservoir, the indicator configured to align with the second end of the housing when the reservoir is the corresponding volume. The volume of the reservoir can be correlated to the fluid pressure in the reservoir being applied by the source of pressurized fluid (e.g., a syringe).

In some embodiments, the housing can define an opening in the second end and the seal member can define a lumen. The fluid pressure regulating device 110 can also include a tube defining a lumen, the tube disposed within the opening of the second end and coupled to the seal member such that fluid can flow through the tube, through the lumen of the seal member, and into the reservoir.

In some embodiments, the fluid pressure regulating device 110 can include a housing and a seal member. The housing can define an interior and can have a first end and a second end. The first end of the housing can be configured to be fluidically coupled to a tube portion. The seal member can be disposed in the interior of the housing and can have a first side and a second side. The first side of the seal member and the housing can collectively define an expandable first reservoir having a first volume. The second side of the seal member and the housing can collectively define a second reservoir having a second volume. The second reservoir is fluidically isolated from the first reservoir. The seal member can be configured to translate within the interior of the housing such that, when the first end of the housing is fluidically coupled to the tube portion such that a lumen of the tube portion is in fluid communication with the reservoir and when a fluid pressure of a fluid in the lumen of the tube portion and the reservoir increases, the fluid can apply a force to the seal member such that the seal member translates toward the second end of the housing and compresses a gas disposed within the second reservoir such that the volume of the first reservoir increases as fluid is received into the first reservoir from the lumen of the tube portion. In some embodiments, when the fluid pressure of the fluid decreases, the gas in the second reservoir can expand and apply a force to the seal member such that fluid is expelled from the first reservoir as the volume of the first reservoir decreases.

Including a fluid pressure regulating device, such as the fluid pressure regulating device 110, in a fluid delivery system, such as the system 100, can result in a volume of fluid being delivered to a patient faster and/or with reduced input force or pressure required. Furthermore, in use cases where the fluid being delivered is blood, the inclusion of the fluid pressure regulating device 110 can reduce hemolysis during infusion. Hemolysis increases with increasing instantaneous flow rates and pressures during flow through intravenous catheters, i.e. with higher fluid shear forces. Thus, converting the pulsatile high-pressure flow associated with, for example, syringe-driven infusion to a more-constant flow with lower instantaneous flow rates can decrease hemolysis.

Figure 2:
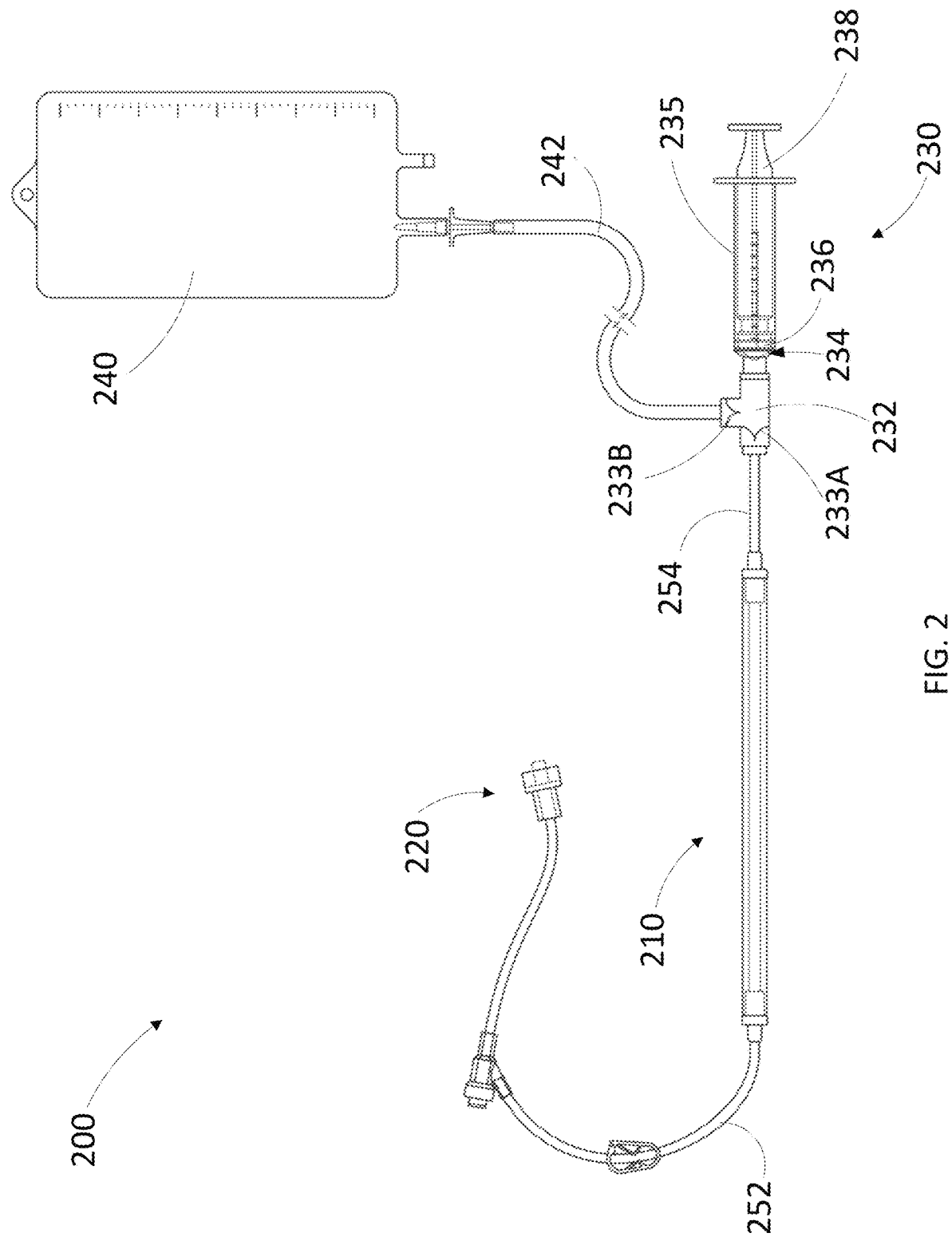
FIG. 2 is a top view of a system, according to an embodiment.

FIG. 2 is a top view of a system 200. The system 200 can be the same or similar in structure and/or function to any of the systems described herein, such as the system 100. For example, the system 200 includes a fluid pressure regulating device 210, a patient access component 220, and a source of pressurized fluid 230. As shown in FIG. 2, the fluid pressure regulating device 210 can be coupled to the patient access component 220 via a first tube portion 252 and the source of pressurized fluid 230 can be coupled to the fluid pressure regulating device 210 via a second tube portion 254. The source of pressurized fluid 230 can be coupled to a source of fluid 240 (e.g., a fluid bag) via a source tube 242 such that the source of fluid 240 can provide fluid (e.g., intravenous fluid or blood) to the source of pressurized fluid 230 such that the source of pressurized fluid can deliver pressurized fluid to the fluid pressure regulating device 210 and the patient access component 220.

The source of pressurized fluid 230 includes a dual check valve assembly 232, a housing 235 (e.g., a syringe barrel), a seal member 236, and a plunger 238. The seal member 236 and the housing 235 can define a reservoir 234. The dual check valve assembly 232 can include a first one-way valve 233A and a second one-way valve 233B. The dual check valve assembly 232 defines an interior and is coupled to the housing 235 such that the interior of the dual check valve assembly 232 is in fluid communication with the reservoir 234. The source of pressurized fluid 230 can be configured such that, when the plunger 238 is being pushed distally (e.g., toward the dual check valve assembly 232) relative to the housing 235 such that the seal member 236 is translated distally, the source of pressurized fluid 230 can deliver fluid through the first one-way valve 233A of the dual check valve assembly 232 such that fluid can be delivered to the patient access component 220 via the second tube portion 254, the expandable reservoir of the fluid pressure regulating device 210, and the first tube portion 252. The source of pressurized fluid 230 can also be configured such that, when the plunger 238 is being translated proximally (e.g., away from the dual check valve assembly 232) relative to the housing 235 such that the seal member 236 is translated proximally, the first one-way valve 233A can fluidically isolate the reservoir 234 from the lumen of the second tube portion 254 and fluid can be drawn from the fluid source 240, through the second one-way valve 233B, and into the reservoir 234. In some embodiments, the source of pressurized fluid 230 can be manually-operated such that the plunger 238 is translated (e.g., pushed and pulled) by a user (e.g., a healthcare provider).

As shown in FIGS. 3A-3C, which are cross-sectional illustrations of the fluid pressure regulating device 210 in various stages of operation, the fluid pressure regulating device 210 includes an outer tube 214 and an inner tube 212. The outer tube 214 can have a first end and a second end and can define a lumen 215. The inner tube 212 can have a first end and a second end and can define an expandable reservoir 213. The expandable reservoir 213 can have a first volume. The inner tube 212 can be disposed within the lumen 215 of the outer tube 214. The first end of the inner tube 212 can be coupled to the first end of the outer tube 214 via a first end connector 216. The second end of the inner tube 212 can be coupled to the second end of the outer tube 214 via a second end connector 218. The inner tube 212 and the outer tube 214 can be coaxially disposed. The first end connector 216 can be configured to be coupled to the first tube portion 252 such that a lumen 253 of the first tube portion 252 is in fluidic communication with the reservoir 213 of the inner tube 212. The second end connector 218 can be configured to be coupled to a second tube portion 254 such that a lumen 255 of the second tube portion 254 is in fluidic communication with the reservoir 213 of the inner tube 212.

The inner tube 212 can include a sidewall portion that is sufficiently compliant such that the inner tube 212 is configured to expand laterally relative to a central axis of the inner tube 212 when a pressure level of a fluid within the reservoir 213 increases such that the reservoir 213 has a second volume greater than the first volume. FIG. 3A shows the reservoir 213 in an initial or first configuration corresponding to the reservoir 213 having the first volume in which the fluid in the reservoir 213 is at a pressure level below that which would cause the inner tube 212 to expand such that the volume of the reservoir 213 increases. The sidewall portion can be resiliently biased toward the first volume such that, when the reservoir 213 has a volume greater than the first volume, as shown in FIG. 3B, the inner tube 212 is configured to apply a force to the fluid within the reservoir 213 to expel the fluid from the reservoir 213 as the pressure level of the fluid within the reservoir 213 decreases.

The outer tube 214 can have a first outermost diameter and can be expandable such that, when the inner tube 212 is expanded such that an outer surface of the inner tube 212 applies pressure to an inner surface of the outer tube 214, the outer tube 214 is configured to expand laterally relative to a central axis of the outer tube. For example, as shown in FIG. 3C, when the inner tube 212 is expanded such that the volume of the reservoir 213 is increased beyond the volume of the reservoir 213 in FIG. 3B, the outer surface of the inner tube 212 can apply a force to the inner surface of the outer tube 214 such that the outer tube 214 expands to an outermost diameter greater than the first outermost diameter. The outer tube 214 can be resiliently biased toward the first outermost diameter and, after the inner tube 212 is expanded such that an outer surface of the inner tube 212 applies pressure to an inner surface of the outer tube 214, the outer tube 214 can apply a force to the outer surface of the inner tube 212 such that the force applied by the inner tube 212 to the fluid within the reservoir includes the force applied by the outer tube 214 to the outer surface of the inner tube 212. When the inner tube 212 is expanding toward the outer tube 214 but not yet contacting the outer tube 214, the fluid pressure regulating device 210 will have a first spring rate. When the inner tube 212 is contacting the outer tube 214 and expanding the outer tube 214, the fluid pressure regulating device 210 will have a second spring rate greater than the first spring rate. Thus, the fluid pressure regulating device 210 can have a linear or progressive spring rate profile, rather than a regressive spring rate, which the inner tube 212 could have without the compliant outer tube 214. The compliance of the outer tube 214 reduces the change in resistance a user may perceive when applying an input force to the source of pressurized fluid 230 such that the change in resistance is gradual rather than sudden. This reduces the chance that the user may falsely perceive the transition as a change in resistance of the fluid path indicating an obstruction or infiltration. The outer tube 214 can also prevent the inner tube 212 from rupturing.

With respect to the properties of the inner tube 212, the spring rate profile of the fluid pressure regulating device 210 can be based, at least in part, on the material durometer or Young's modulus of the inner tube 212, on the inner diameter of the inner tube 212 in the initial, unexpanded state, on the thickness of the wall of the inner tube 212, and on the length of the inner tube 212.

In one exemplary embodiment, the inner tube 212 can have an inner diameter of between about 0.1" and 0.25" in an initial, unexpanded state. If the inner diameter is less than about 0.1", the wall thickness is required to be too thin or the material too soft to be operable to achieve the desired spring rate profile. In some embodiments, the spring rate of the inner tube 212 can be, for example, about 6 psi/ml.

The surface tension of aqueous liquids may be low enough to allow air to be trapped within the expandable reservoir 213 defined by the inner tube 212 during the priming process (filling all fluid-containing portions of the system before use on the patient) if the diameter of the expandable reservoir is too large, posing a danger to the patient if the trapped air subsequently escapes (e.g., if the tubing reservoir is inadvertently vertically-oriented during use) and travels in to the patient's vasculature system. Thus, in some embodiments, the inner diameter of the inner tube 212 in the initial, unexpanded configuration can be sufficiently small (e.g., below a threshold diameter) such that no air will be trapped in the reservoir during priming of the system 200, regardless of the orientation of the inner tube 212 during priming. Thus, a user (e.g., a clinician) will not need to manipulate the fluid pressure regulating device 210 during and/or after priming to avoid air being trapped in the inner tube 212. For example, the inner diameter of the inner tube 212 in the initial, unexpanded configuration can be equal to or less than about 0.25 inches. In some embodiments, the inner diameter of the inner tube 212 may be sufficiently large such that the inner tube 212 must be disposed vertically during priming to prevent a bubble of trapped air from remaining in the expandable reservoir 213. In some embodiments, the inner diameter of the inner tube 212 in the initial, unexpanded configuration can be, for example, 0.1". In some embodiments, the inner diameter of the inner tube 212 in the initial, unexpanded state can be between about 0.1" and about 0.19".

Figure 16:
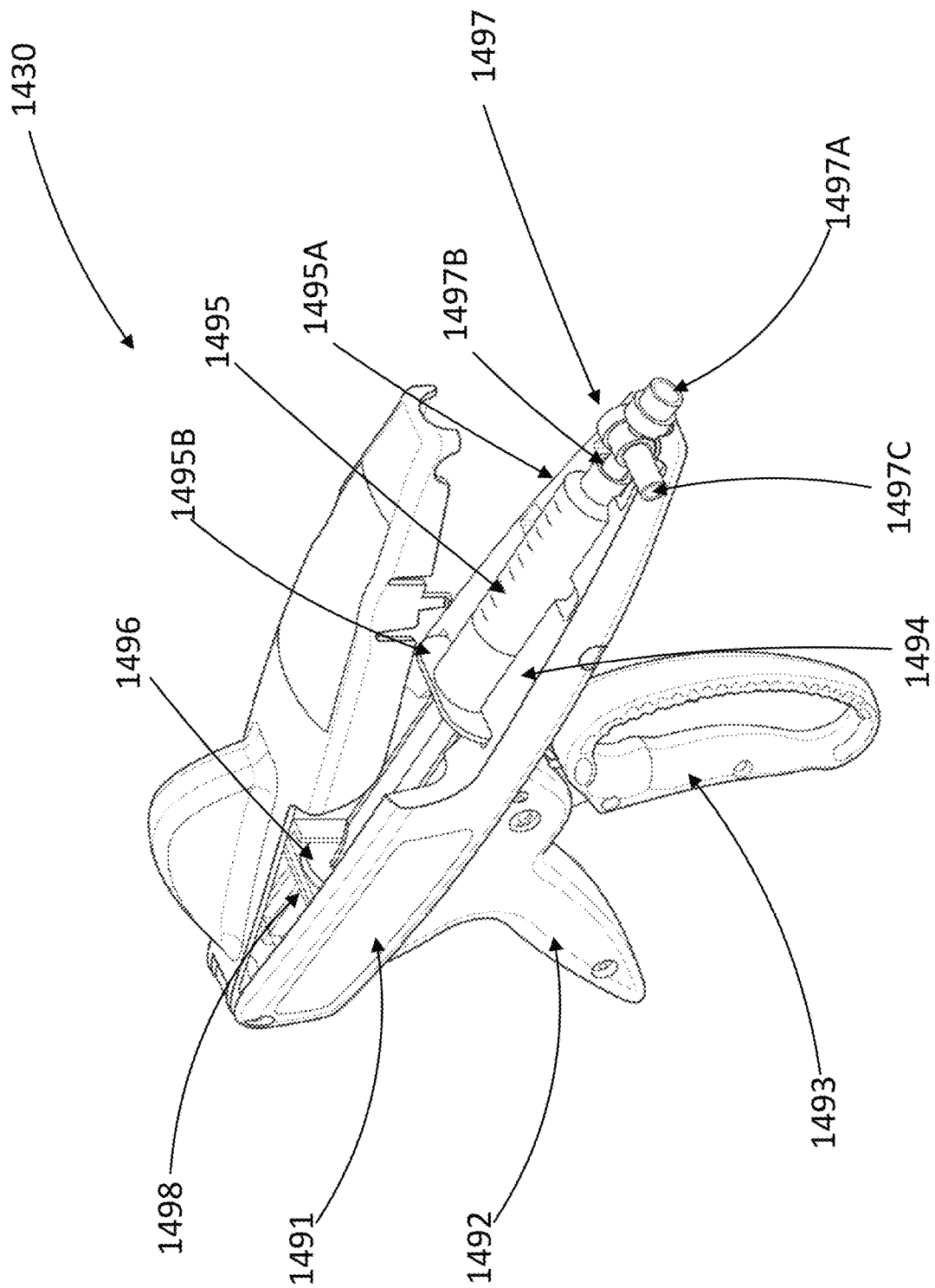
FIG. 16 is a perspective view of an exemplary source of pressurized fluid, according to an embodiment.

In some embodiments, the fluid pressure regulating device 210, the source of pressurized fluid 230, the first tube portion 252, and the patient access component 220 can be configured (based at least in part on a spring rate and internal volume of the fluid pressure regulating device 210, a refill time period of the source of pressurized fluid 230, a volume and pressure of fluid expelled from the source of pressurized fluid, and an inner diameter of each of the first tube portion 252 and the patient access component 220) such that the time duration of the fluid pressure regulating device 210 transitioning from a second or expanded configuration to the first or unexpanded configuration (e.g., by expelling fluid into the first tube portion 252 and the patient access component 220) is substantially the same as the time duration of refilling the source of pressurized fluid 230 (e.g., refilling the housing 235 from the fluid source 240). For example, the source of pressurized fluid 230 can include a manually-operated infusion device such as is shown in FIG. 16 and described below. The plunger 238 can be transitioned (e.g., retracted) from a distal-most position to a proximal-most position within the housing 235 to draw fluid into the housing 235 (e.g., under control of an actuator of the device such as a trigger) within a duration of time that is substantially similar to the duration of time in which the fluid pressure regulating device 210 transitions from the second or expanded configuration to the first or unexpanded configuration. Thus, refilling the source of pressurized fluid 230 from the fluid source 240 can have substantially the same time duration as transitioning the fluid pressure regulating device 210 from the second or expanded configuration to the first or unexpanded configuration and no waiting period is required after refilling the source of pressurized fluid 230 or expelling fluid from the fluid pressure regulating device 210 before providing additional pressurized fluid from the source of pressurized fluid 230 to the fluid pressure regulating device 210. The first tube portion 252 can be or include, for example, a 20 gauge catheter, a 22 gauge catheter, and/or a 16 gauge catheter.

The inner tube 212 can be formed of any suitable material, such as, for example, translucent or transparent thermoplastic elastomers, silicone, and PVC grades with durometers between 30A and 70A. The inner tube 212 is preferably translucent or transparent so that air bubbles can be visualized inside the inner tube 212. If the inner tube 212 is softer than 30A, the manufacturing difficulty increases because the material is too soft and tacky. If the inner tube 212 is harder than 70A, the inner diameter of the inner tube 212 has to be too high or the wall thickness of the inner tube 212 too small than is practical to achieve the desired spring rate profile.

The inner tube 212 can have any suitable length. For example, the length can range between about 4" and about 24". If the length is shorter than 4", the inner tube 212 must have an excessively thin wall thickness or excessively low durometer to achieve the desired spring rate profile. If the inner tube 212 is longer than 24", the inner tube 212 may become unwieldy for the user.

With respect to properties of the outer tube 214, the spring rate profile of the fluid pressure regulating device 210 can be based, at least in part, on the inner diameter of the outer tube 214 when the fluid pressure regulating device 210 is in the unexpanded, initial state (and thus, the gap between the outer surface of the inner tube 212 and the inner surface of the outer tube 214), on the material durometer (Young's modulus) of the outer tube 214, and on the wall thickness of the outer tube 214.

In an exemplary embodiment, the radial gap between the inner tube 212 and the outer tube 214 may range between, for example, about 0.03" and about 0.125". If the gap is less than 0.03", the inner tube 212 has very little room for expansion before engaging with the inner surface of the outer tube 214, causing the spring rate to increase early in the delivery cycle from the source of pressurized fluid 230 and minimizing the force reduction effect for the user. If the gap is greater than 0.125", the inner tube 212 may begin to yield prior to contacting the inner surface of the outer tube 214, causing the inner tube 212 to rupture. The durometer of the outer tube 214 can range between 50A and 90A and the wall thickness can range between about 0.03" and 0.125". If the outer tube 214 is too soft and/or thin-walled, the outer tube 214 will not adequately contain the inner tube 212 and will allow the inner tube 212 to expand significantly. If the outer tube 214 is too hard and/or thick-walled, the outer tube 214 would behave more like a rigid tube, making the spring rate transition too abrupt and potentially confusing the user as to whether an obstruction of infiltration has occurred.

Although not shown, in some embodiments, rather than the outer tube 214 being expandable and resiliently biased, the outer tube 214 can be rigid such that, when the inner tube 212 is expanded such that an outer surface of the inner tube 212 applies pressure to an inner surface of the outer tube 214, the outer tube 214 prevents further lateral expansion of the inner tube 212.

In some embodiments, the fluid pressure regulating device 210 can include a vent (not shown) such that air disposed between the outer tube 214 and the inner tube 212 can travel into and/or out of the lumen 215. In some embodiments, the lumen 215 is fluidically isolated from an area outside of the fluid pressure regulating device 210.

Figure 3D:
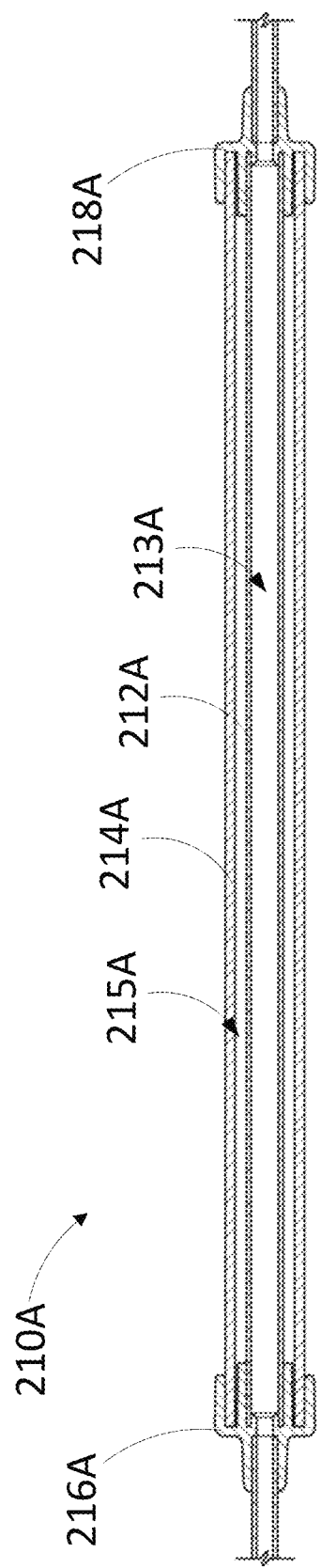
FIG. 3D is a cross-sectional illustration of a fluid pressure regulating device, according to an embodiment.

In some embodiments, the first end connector and the second end connector of the fluid pressure regulating device can each define recesses to receive the first end and the second end of the outer tube, respectively. For example, FIG. 3D is a cross-sectional illustration of a fluid pressure regulating device 210A. The fluid pressure regulating device 210A can be the same or similar in structure and/or function to the fluid pressure regulating device 210 described above with respect to FIGS. 3A-3C. For example, the fluid pressure regulating device 210A includes an outer tube 214A and an inner tube 212A that can be the same or similar in structure and/or function to the outer tube 214 and the inner tube 212. The outer tube 214A can have a first end and a second end and can define a lumen 215A. The inner tube 212A can have a first end and a second end and can define an expandable reservoir 213A.

As shown in FIG. 3D, the first end of the inner tube 212A can be coupled to the first end of the outer tube 214A via a first end connector 216A. The second end of the inner tube 212A can be coupled to the second end of the outer tube 214A via a second end connector 218A. The first end connector 216A can define a first circular recess to receive the first end of the outer tube 214A and a second circular recess to receive the first end of the inner tube 212A. Additionally, the second end connector 218A can define a first circular recess to receive the second end of the outer tube 214A and a second circular recess to receive the second end of the inner tube 212A. The second circular recesses of each of the first end connector 216A and the second end connector 218A can result in reduced stress on the connection between the outer tube 214A and the first end connector 216A and/or the second end connector 218A (e.g., when the reservoir 213A and/or the lumen 215A are filled with pressurized fluid). The first circular recess and the second circular recess of the first end connector 216A and the first circular recess and the second circular recess of the second end connector 216A can be concentric. The first end connector 216A can be configured to be coupled to a first tube portion (such as, for example, the first tube portion 252) such that a lumen of the first tube portion is in fluidic communication with the reservoir 213A of the inner tube 212A. The second end connector 218A can be configured to be coupled to a second tube portion (such as, for example, the second tube portion 254) such that a lumen of the second tube portion is in fluidic communication with the reservoir 213A of the inner tube 212A.

Figure 6:
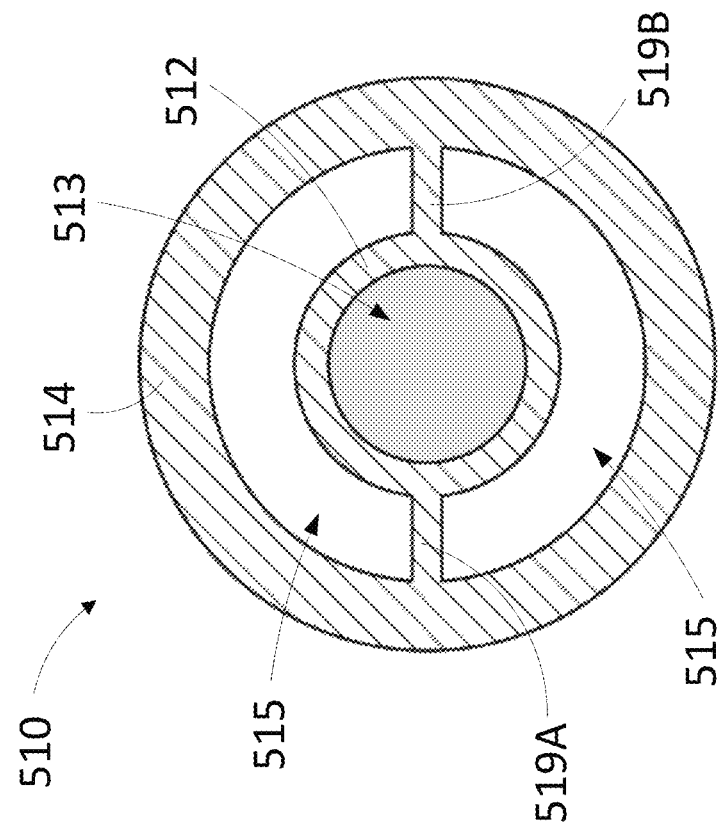
FIG. 6 is a cross-sectional illustration of a fluid pressure regulating device, according to an embodiment.

In some embodiments, the fluid pressure regulating device can include an inner tube and an outer tube, and be manufactured as a single multi-lumen extrusion. For example, FIG. 6 is a cross-sectional illustration of a fluid pressure regulating device 510. The fluid pressure regulating device 510 can be the same or similar in structure and/or function to the fluid pressure regulating device 210 described above with reference to FIGS. 2-3D. For example, the fluid pressure regulating device 510 includes an outer tube 514 and an inner tube 512. The outer tube 514 can define a lumen 515. The inner tube 512 can define an expandable reservoir 513. The expandable reservoir 513 can have a first volume. As shown in FIG. 6, the inner tube 512 can be disposed within the lumen 515 of the outer tube 514 and the inner tube 512 and the outer tube 514 can be coaxially disposed. The inner tube 512 can be coupled to the outer tube 514 via connection portions 519A, 519B such that the inner tube 512 and the outer tube 514 can be formed as a single multi-lumen extrusion. In some embodiments, the connecting portions 519A, 519B can each have the same length as the inner tube 512 and the outer tube 514 such that the lumen 515 is divided into portions. In some embodiments, the connecting portions 519A, 519B can be have a shorter length than the length of the inner tube 512 and/or the outer tube 514. Although two connecting portions 519A, 519B are shown, the fluid pressure regulating device 510 can include any suitable number of connecting portions (e.g., one, three, or four).

Figure 7:
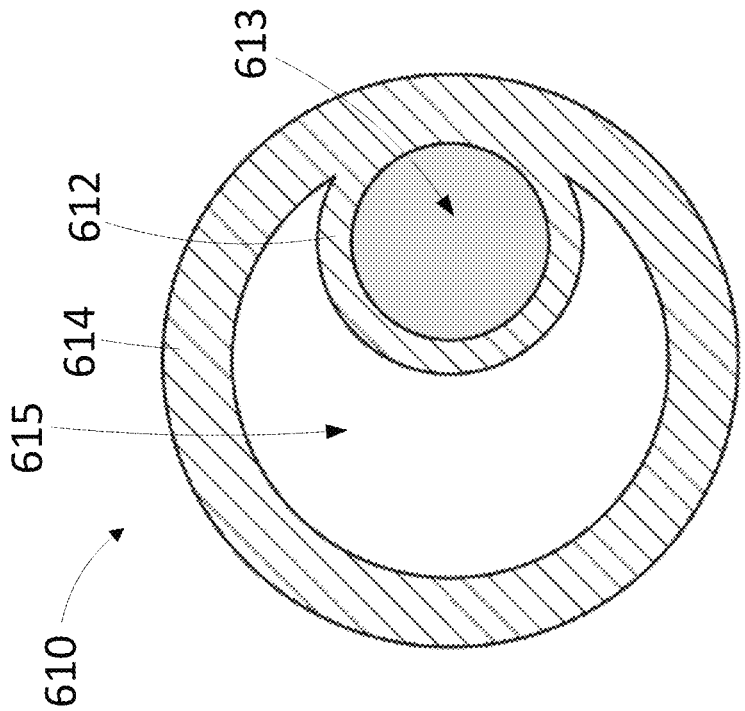
FIG. 7 is a cross-sectional illustration of a fluid pressure regulating device, according to an embodiment.

In some embodiments, the inner tube and the outer tube of the fluid pressure regulating device can be manufactured as a single multi-lumen extrusion such that the inner tube and the outer tube share a wall. For example, FIG. 7 is a cross-sectional illustration of a fluid pressure regulating device 610. The fluid pressure regulating device 610 can be the same or similar in structure and/or function to the fluid pressure regulating device 210 described above with reference to FIGS. 2-3C. For example, the fluid pressure regulating device 610 includes an outer tube 614 and an inner tube 612. The inner tube 612 can define an expandable reservoir 613. The expandable reservoir 613 can have a first volume. As shown in FIG. 7, the inner tube 612 and the outer tube 614 can share a wall such that an inner surface of the outer tube 614 and an outer surface of the inner tube collectively define a lumen 615.

Figure 8:
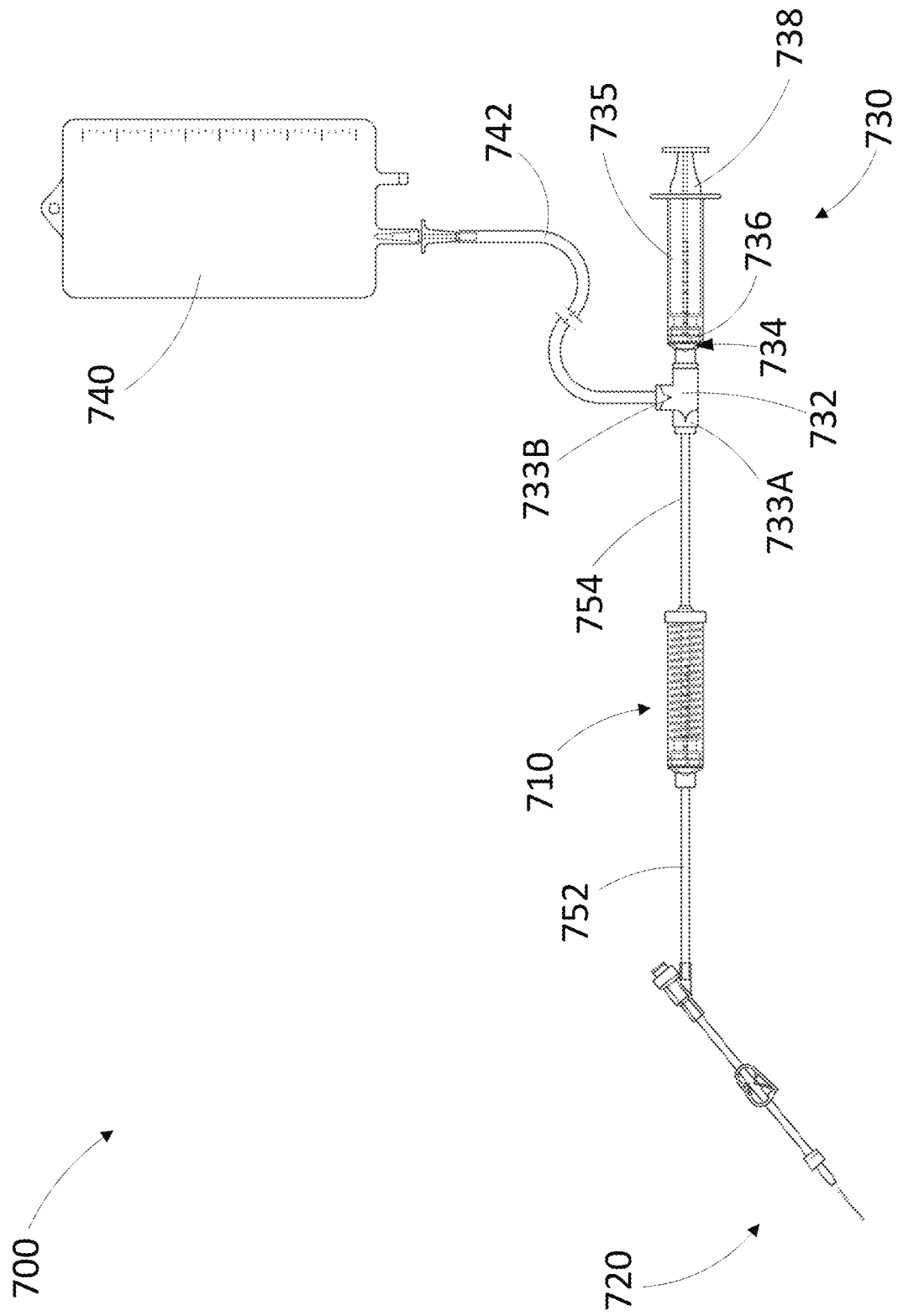
FIG. 8 is a top view of a system, according to an embodiment.

FIG. 8 is a top view of a system 700. The system 700 can be the same or similar in structure and/or function to any of the systems described herein, such as the system 100 and/or the system 200. For example, the system 700 includes a fluid pressure regulating device 710, a patient access component 720, and a source of pressurized fluid 730. As shown in FIG. 8, the fluid pressure regulating device 710 can be coupled to the patient access component 720 via a first tube portion 752 and the source of pressurized fluid 730 can be coupled to the fluid pressure regulating device 710 via a second tube portion 754. The source of pressurized fluid 730 can be coupled to a source of fluid 740 (e.g., a fluid bag) via a source tube 742 such that the source of fluid 740 can provide fluid (e.g., intravenous fluid or blood) to the source of pressurized fluid 730 such that the source of pressurized fluid can deliver pressurized fluid to the fluid pressure regulating device 710 and the patient access component 720.

The source of pressurized fluid 730 can be the same or similar in structure and/or function to the source of pressurized fluid 230 described above with respect to system 200. For example, the source of pressurized fluid 730 can include a dual check valve assembly 732, a housing 735 (e.g., a syringe barrel), a seal member 736, and a plunger 738. The seal member 736 and the housing 735 can define a reservoir 734. The dual check valve assembly 732 can include a first one-way valve 733A and a second one-way valve 733B. The dual check valve assembly 232 defines an interior and is coupled to the housing 735 such that the interior of the dual check valve assembly 732 is in fluid communication with the reservoir 734. The source of pressurized fluid 730 can function in use the same way as described above with respect to the system 200.

As shown in FIGS. 9A and 9B, which are cross-sectional illustrations of the fluid pressure regulating device 710 in an initial configuration and a larger volume configuration, respectively, the fluid pressure regulating device 710 includes a housing 761, a spring member 766, and a seal member 760. The housing 761 can define an interior and can have a first end 762A and a second end 762B. The first end 762A of the housing 761 can be configured to be fluidically coupled to the first tube portion 752 (shown in FIG. 8). The spring member 766 can be disposed within the interior of the housing 761 and can have a first end 769A and a second end 769B. The second end 769B of the spring member 766 can be coupled to the second end 762B of the housing 761. In some embodiments, the second end 762B of the housing 761 includes an end cap 763 and the second end 769B of the spring member 766 can be coupled to the end cap 763. The spring member 766 can be resiliently biased toward an expanded configuration. The seal member 760 can be disposed in the interior of the housing 761 and coupled to the first end 769A of the spring member 766. The seal member 760 and the housing 761 can collectively define an expandable reservoir 764 having a first volume. The spring member 766 can be a coil spring, a wave spring, or an air spring. In some embodiments, the second end 762B of the housing 761 can be rigidly coupled to the source of pressurized fluid 730 (without the second tube portion 754). In such an embodiment, both the fluid pressure regulating device 710 and the source of pressurized fluid 730 can be purged of air simultaneously by pointing the first end 762A of the housing 761 of the fluid pressure regulating device 710 upward such that the distal ends of both the fluid pressure regulating device 710 and the source of pressurized fluid 730 are pointing upward prior to purging.

As shown in FIGS. 9A and 9B, the housing 761 defines an opening in the second end 762B (e.g., in the end cap 763) and the seal member 760 defines a lumen 765. The fluid pressure regulating device 710 can include a flexible tube 767 defining a lumen. The tube 767 can be disposed within the opening of the second end 762B and coupled to the seal member 760 such that fluid can flow through the tube 767, through the lumen 765 of the seal member 760, and into the reservoir 764. Thus, the fluid pressure regulating device 710 can be coupled to the second tube portion 754 such that fluid can be delivered from the source of pressurized fluid 730, through the second tube portion 754, through the tube 767, through the lumen 765, and into the reservoir 764. From the reservoir 764, fluid can flow into the first tube portion 752 when the fluid pressure regulating device 710 is coupled to the first tube portion 752. As shown in FIG. 9B, the seal member 760 can be configured to translate within the interior of the housing 761 such that, when a fluid pressure of a fluid in the tube portion 752 and the reservoir 764 increases (e.g., due to the delivery of pressurized fluid from the source of pressurized fluid 730 via the tube 767 and the lumen 765), the fluid applies a force to the seal member 760 such that the seal member 760 translates toward the second end 762B of the housing 761 and the spring member 766 transitions from the expanded position to a compressed position such that the volume of the reservoir 764 increases from the first volume to a second volume greater than the first volume as fluid is received into the reservoir 764. Furthermore, when the fluid pressure of the fluid in the tube portion 752 and the reservoir 764 decreases, the spring member 766 transitions from the retracted position to the expanded position such that the volume of the reservoir 764 decreases as fluid is expelled from the reservoir 764 into the tube portion 752. In some embodiments, the spring member 766 can have a progressive spring rate. For example, the spring member 766 can include multiple concentric coil springs having different spring rates and/or can include multiple coil springs of different spring rates arranged in series.

In some embodiments, the flexible tube 767 can be formed as a coiled tube such that the tube 767 can expand and retract while minimizing the likelihood that the tube 767 will kink. Furthermore, the fluid pressure regulating device 710 that is in-line with the second tube portion 754 and the first tube portion 752 can avoid shear forces associated with fluid changing directions when compared to coupling a fluid pressure regulating device 710 to a fluid path to divert some of the fluid traveling through a fluid path.

In an exemplary embodiment, the inner diameter of the housing 761 may be between about 0.3" and about 1.5". If the inner diameter of the housing 761 is too small (e.g., smaller than about 0.3"), the housing 761 may need to be excessively long to store sufficient fluid. If the inner diameter of the housing 761 is too large (e.g., greater than about 1.5"), an impractical amount of spring force may be needed to achieve the desired spring rate profile.

Figure 10:
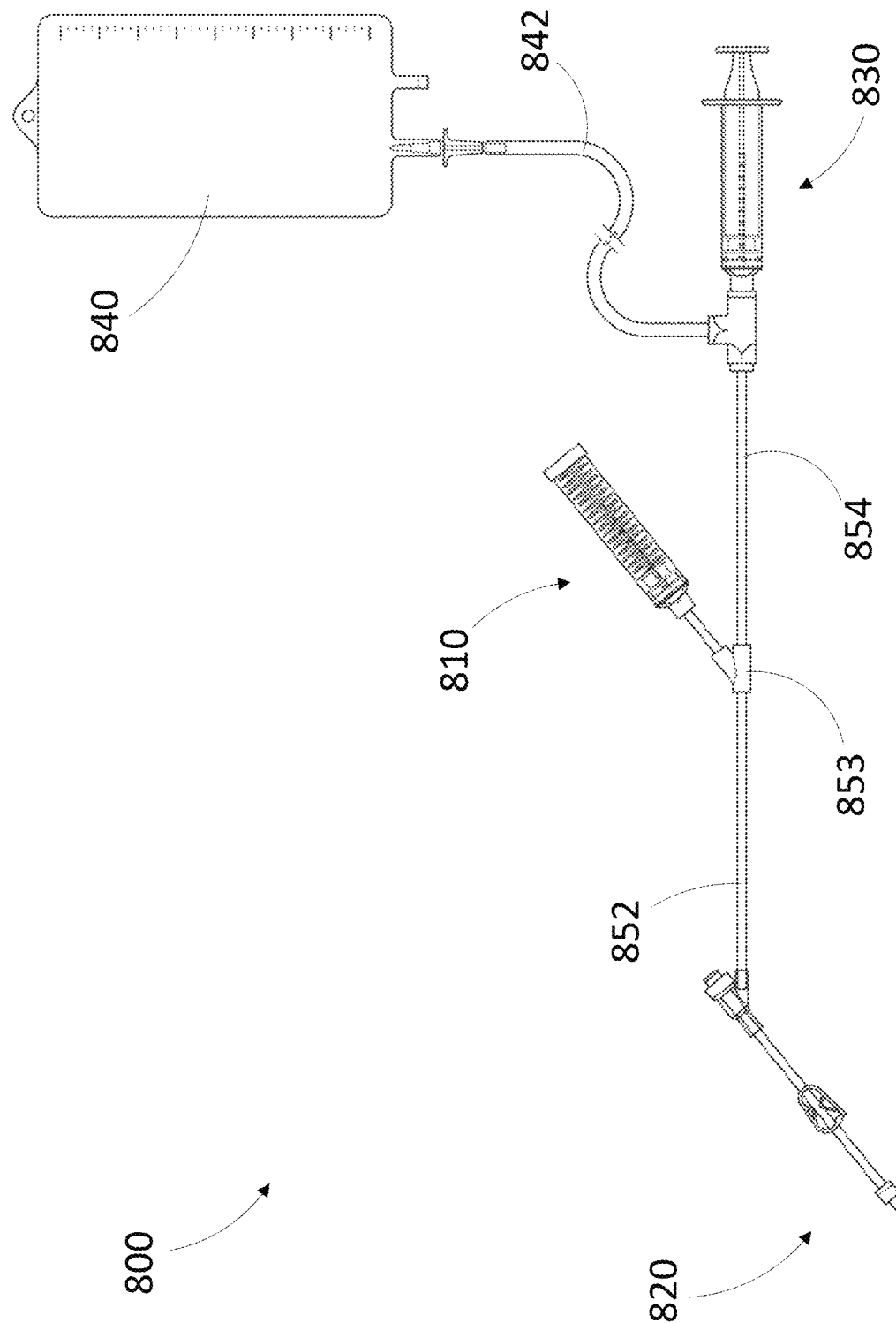
FIG. 10 is a top view of a system, according to an embodiment.

In some embodiments, rather than including a fluid pressure regulating device in-line with a first tube portion and a second tube portion such that fluid is delivered from the source of pressurized fluid to the patient access component through the fluid pressure regulating device, a fluid pressure regulating device can be coupled to a tube portion peripherally or at an angle such that a portion of the fluid delivered from the source of pressurized fluid is diverted into a reservoir of the fluid pressure regulating device. For example, FIG. 10 shows a top view of a system 800. The system 800 can be the same or similar in structure and/or function to any of the systems described herein, such as the system 100 and/or the system 200. For example, the system 800 includes a fluid pressure regulating device 810, a patient access component 820, and a source of pressurized fluid 830. As shown in FIG. 10, the fluid pressure regulating device 810 can be coupled to the patient access component 820 via a fluid connector 853 and a first tube portion 852 and the source of pressurized fluid 830 can be coupled to the fluid pressure regulating device 810 via the fluid connector 853 and a second tube portion 854. The fluid connector 853 can be, for example, a Y-connector. The source of pressurized fluid 830 can be coupled to a source of fluid 840 (e.g., a fluid bag) via a source tube 842 such that the source of fluid 840 can provide fluid (e.g., intravenous fluid or blood) to the source of pressurized fluid 830 such that the source of pressurized fluid can deliver pressurized fluid to the fluid pressure regulating device 810 and the patient access component 820. Although the fluid connector 853 is shown as a Y-connector in FIG. 10, in some embodiments the fluid connector 853 can be a T-connector.

Figure 11:
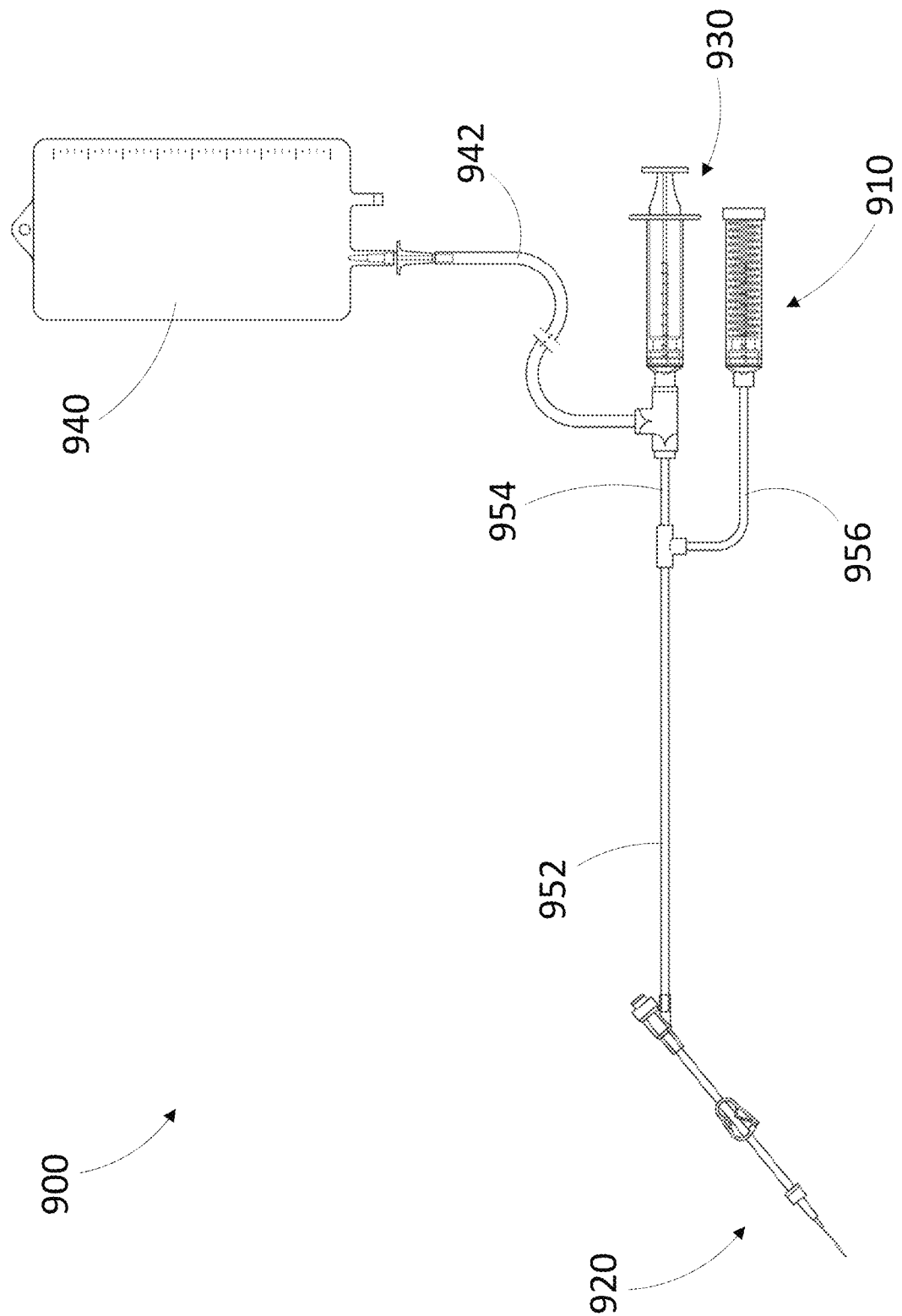
FIG. 11 is a top view of a system, according to an embodiment.

FIG. 11 is a top view of a system 900. The system 900 can be the same or similar in structure and/or function to any of the systems described herein, such as the system 100 and/or the system 200. For example, the system 900 includes a fluid pressure regulating device 910, a patient access component 920, and a source of pressurized fluid 930. As shown in FIG. 11, the fluid pressure regulating device 910 can be coupled to the patient access component 920 via a third tube portion 956 a first tube portion 952 and the source of pressurized fluid 930 can be coupled to the fluid pressure regulating device 910 via the third tube portion 956 and a second tube portion 954. Thus, the fluid pressure regulating device 910 can be arranged in parallel relative to the source of pressurized fluid 930 such that interaction between the user, the fluid pressure regulating device 910, and the source of pressurized fluid 930 can be improved (e.g., less unwieldy and/or more efficient). The source of pressurized fluid 930 can be coupled to a source of fluid 940 (e.g., a fluid bag) via a source tube 942 such that the source of fluid 940 can provide fluid (e.g., intravenous fluid or blood) to the source of pressurized fluid 930 such that the source of pressurized fluid can deliver pressurized fluid to the fluid pressure regulating device 910 and the patient access component 920. In some embodiments, the source of pressurized fluid 930 and the fluid pressure regulating device 910 can be contained within a common cartridge.

FIG. 12 is a side view of a fluid pressure regulating device 1010. The fluid pressure regulating device 1010 can be the same or similar in structure and/or function to any of the fluid pressure regulating devices described herein, such as, for example, the fluid pressure regulating device 810 and/or the fluid pressure regulating device 910. The fluid pressure regulating device 1010 can include a housing 1061, a spring member 1066, and a seal member 1060. The housing 1061 can define an interior and can have a first end 1062A and a second end 1062B. The first end 1062A of the housing 1061 can be configured to be fluidically coupled to a first tube portion (such as the first tube portion 852 shown in FIG. 10) and a second tube portion (such as the second tube portion 854 shown in FIG. 10) via a fluid connector (such as the fluid connector 853 shown in FIG. 10). The spring member 1066 can be disposed within the interior of the housing 1061 and can have a first end 1069A and a second end 1069B. The second end 1069B of the spring member 1066 can be coupled to the second end 1062B of the housing 1061. In some embodiments, the second end 1062B of the housing 1061 includes an end cap 1063 and the second end 1069B of the spring member 1066 can be coupled to the end cap 1063. The spring member 1066 can be resiliently biased toward an expanded configuration. The seal member 1060 can be disposed in the interior of the housing 1061 and coupled to the first end 1069A of the spring member 1066. The seal member 1060 and the housing 1061 can collectively define an expandable reservoir 1064 having a first volume. The spring member 1066 can be a coil spring or a wave spring.

The seal member 1060 can be configured to translate within the interior of the housing 1061 such that, when a fluid pressure of a fluid in a lumen of a tube portion fluidically coupled to the reservoir 1064 (e.g., the first tube portion 852 shown in FIG. 10) and the reservoir 1064 increases (e.g., due to the delivery of pressurized fluid from a source of pressurized fluid such as the source of pressurized fluid 830), the fluid applies a force to the seal member 1060 such that the seal member 1060 translates toward the second end 1062B of the housing 1061 and the spring member 1066 transitions from the expanded position to a compressed position such that the volume of the reservoir 1064 increases from the first volume to a second volume greater than the first volume as fluid is received into the reservoir 1064. Furthermore, when the fluid pressure of the fluid in the tube portion 1052 and the reservoir 1064 decreases, the spring member 1066 transitions from the retracted position to the expanded position such that the volume of the reservoir 1064 decreases as fluid is expelled from the reservoir 1064 into the tube portion 1052.

In an exemplary embodiment, the inner diameter of the housing 1061 may be between about 0.3" and about 1.5". If the inner diameter of the housing 1061 is too small (e.g., smaller than about 0.3"), the housing 1061 may need to be excessively long to store sufficient fluid. If the inner diameter of the housing 1061 is too large (e.g., greater than about 1.5"), an impractical amount of spring force may be needed to achieve the desired spring rate profile.

In some embodiments, a fluid pressure regulating device can include one or more externally-visible indicators such that a user can more easily determine a state of the fluid pressure regulating device (e.g., a volume of an expandable reservoir corresponding to a pressure level of the fluid in the expandable reservoir). Such an indicator of pressure may be useful so that the user can properly time the fluid delivery from a source of pressurized fluid (e.g., syringe plunger compressions). For example, especially when a patient access component or a tube portion of a system includes a lumen having a small diameter, a fluid pressure regulating device of the system may take a significant amount of time to decrease in volume to an initial configuration while expelling fluid. Thus, an externally-visible indicator of a pressure level can indicate to the user when to initiate the next delivery cycle (e.g., near or at the time the fluid pressure regulating device has returned to its initial configuration). Such an externally-visible indicator of pressure level may also be used for blood transfusions or the infusion of blood products through any of the systems described herein such that the user can prevent the fluid pressure level within an expandable reservoir and/or tube portion from increasing to the point of potentially damaging red blood cells. For example, FIG. 13 is a side view of a fluid pressure regulating device 1110. The fluid pressure regulating device 1110 can be the same or similar in structure and/or function to the fluid pressure regulating device 1010 shown and described above with respect to FIG. 12. For example, the fluid pressure regulating device 1110 can include a housing 1161, a spring member 1166, and a seal member 1160. The housing 1161 can define an interior and can have a first end 1162A and a second end 1162B. The first end 1162A of the housing 1161 can be configured to be fluidically coupled to a first tube portion (such as the first tube portion 852 shown in FIG. 10) and a second tube portion (such as the second tube portion 854 shown in FIG. 10) via a fluid connector (such as the fluid connector 853 shown in FIG. 10). The spring member 1166 can be disposed within the interior of the housing 1161 and can have a first end 1169A and a second end 1169B. The second end 1169B of the spring member 1166 can be coupled to the second end 1162B of the housing 1161. In some embodiments, the second end 1162B of the housing 1161 includes an end cap 1163 and the second end 1169B of the spring member 1166 can be coupled to the end cap 1163. The spring member 1166 can be resiliently biased toward an expanded configuration. The seal member 1160 can be disposed in the interior of the housing 1161 and coupled to the first end 1169A of the spring member 1166. The seal member 1160 and the housing 1161 can collectively define an expandable reservoir 1164 having a first volume. The spring member 1166 can be a coil spring or a wave spring.

The seal member 1160 can be configured to translate within the interior of the housing 1161 such that, when a fluid pressure of a fluid in a lumen of a tube portion fluidically coupled to the reservoir 1164 (e.g., the first tube portion 852 shown in FIG. 10) and the reservoir 1164 increases (e.g., due to the delivery of pressurized fluid from a source of pressurized fluid such as the source of pressurized fluid 830), the fluid applies a force to the seal member 1160 such that the seal member 1160 translates toward the second end 1162B of the housing 1161 and the spring member 1166 transitions from the expanded position to a compressed position such that the volume of the reservoir 1164 increases from the first volume to a second volume greater than the first volume as fluid is received into the reservoir 1164. Furthermore, when the fluid pressure of the fluid in the tube portion 1152 and the reservoir 1164 decreases, the spring member 1166 transitions from the retracted position to the expanded position such that the volume of the reservoir 1164 decreases as fluid is expelled from the reservoir 1164 into the tube portion 1152.

The housing 1161 can be transparent and can have a number of discrete sections identified by being formed of different colors and/or patterns. For example, the housing 1161 can have a first section 1139A, a second section 1139B, and a third section 1139C. The first section 1139A can be, for example, tinted green. The second section 1139B can be, for example, tinted yellow. The third section 1139C can be, for example, tinted red. Thus, in use, the user can see the seal member 1160 through the wall of the housing 1161. The user can identify whether the pressure level of the fluid in the reservoir 1164 and a tube portion to which the fluid pressure regulating device 1110 is coupled is, for example, low, medium, or high based on the position of the seal member 1160 within the housing 1161 relative to the first section 1139A, the second section 1139B, and the third section 1139C. When the user identifies the pressure level as medium and/or high, in some embodiments the user may delay expelling additional fluid into the tube portion coupled to the fluid pressure regulating device 1110 (e.g., delay compressing a syringe plunger) or reduce the rate of expelling additional fluid until the pressure level has dropped and/or may check a system including the fluid pressure regulating device 1110 for obstructions or infiltration. While the housing 1161 is shown as having qualitative markings in the form of colored sections, in some embodiments the housing 1161 can include qualitative graduations. Additionally, while shown with respect to a fluid pressure regulating device 1110 configured to be attached peripherally to a fluid path such that fluid enters and exits the fluid reservoir 1164 through an opening in the first end 1162A of the housing 1161, any of the fluid pressure regulating devices described herein may include similar indicators of a fluid pressure level in the reservoir. For example, the fluid pressure regulating device 710 shown in FIG. 8 may include similar indicators as described with respect to the fluid pressure regulating device 1110.

In some embodiments, rather than the housing including indicators such as colored portions, the seal member can include one or more indicators. For example, FIGS. 14A and 14B are side view of a fluid pressure regulating device 1210 in a first configuration and a second configuration, respectively. The fluid pressure regulating device 1210 can be the same or similar in structure and/or function to any of the fluid pressure regulating devices described herein, such as the fluid pressure regulating device 1010 and/or the fluid pressure regulating device 1110. For example, the fluid pressure regulating device 1210 can include a housing 1261, a spring member 1266, and a seal member 1260. The housing 1261 can define an interior and can have a first end 1262A and a second end 1262B. The first end 1262A of the housing 1261 can be configured to be fluidically coupled to a first tube portion (such as the first tube portion 852 shown in FIG. 10) and a second tube portion (such as the second tube portion 854 shown in FIG. 10) via a fluid connector (such as the fluid connector 853 shown in FIG. 10). The spring member 1266 can be disposed within the interior of the housing 1261 and can have a first end 1269A and a second end 1269B. The second end 1269B of the spring member 1266 can be coupled to the second end 1262B of the housing 1261. In some embodiments, the second end 1262B of the housing 1261 includes an end cap 1263 and the second end 1269B of the spring member 1266 can be coupled to the end cap 1263. The spring member 1266 can be resiliently biased toward an expanded configuration. The seal member 1260 can be disposed in the interior of the housing 1261 and coupled to the first end 1269A of the spring member 1266. The seal member 1260 and the housing 1261 can collectively define an expandable reservoir 1264 having a first volume. The spring member 1266 can be a coil spring or a wave spring.

The seal member 1260 can be configured to translate within the interior of the housing 1261 such that, when a fluid pressure of a fluid in a lumen of a tube portion fluidically coupled to the reservoir 1264 (e.g., the first tube portion 852 shown in FIG. 10) and the reservoir 1264 increases (e.g., due to the delivery of pressurized fluid from a source of pressurized fluid such as the source of pressurized fluid 830), the fluid applies a force to the seal member 1260 such that the seal member 1260 translates toward the second end 1262B of the housing 1261 and the spring member 1266 transitions from the expanded position to a compressed position such that the volume of the reservoir 1264 increases from the first volume to a second volume greater than the first volume as fluid is received into the reservoir 1264. Furthermore, when the fluid pressure of the fluid in the reservoir 1264 decreases, the spring member 1266 transitions from the retracted position to the expanded position such that the volume of the reservoir 1264 decreases as fluid is expelled from the reservoir 1264 into the tube portion 1252.

In an exemplary embodiment, the inner diameter of the housing 1261 may be between about 0.3" and about 1.5". If the inner diameter of the housing 1261 is too small (e.g., smaller than about 0.3"), the housing 1261 may need to be excessively long to store sufficient fluid. If the inner diameter of the housing 1261 is too large (e.g., greater than about 1.5"), an impractical amount of spring force may be needed to achieve the desired spring rate profile.

As shown in FIG. 14A, the housing 1261 can define an opening 1267 in the second end 1262B (e.g., in the end cap 1263) and the seal member 1260 includes an extending member 1267 extending away from the first end 1262A of the housing 1261. In some embodiments, the extending member 1267 may be disposed completely within the housing 1261 when the volume of the reservoir 1264 is the first volume (as shown in FIG. 14A) and the extending member 1267 can project a distance from the second end 1262B of the housing 1261 when the reservoir 1264 is a second volume greater than the first volume (as shown in FIG. 14B). In some embodiments, the extending member 1267 can extend through the opening 1267 in the second end 1262B of the housing 1261 and project a first distance from the second end 1262B of the housing 1261 when the volume of the reservoir 1264 is the first volume. The extending member 1267 can project a second distance from the second end 1262B of the housing 1261 when the reservoir 1264 is a second volume greater than the first volume.

As shown in FIGS. 14A and 14B, the extending member 1267 can include a number of indicators in the form of discrete sections identified by being formed of different colors. For example, the extending member 1267 can have a first section 1267A, a second section 1267B, and a third section 1267C. The first section 1267A can be, for example, red. The second section 1267B can be, for example, yellow. The third section 1267C can be, for example, green.

Each of the colored sections of the extending member 1267 can correspond to a volume or volume range of the reservoir 1264 such that each of the colored sections is configured to align with the second end 1262B of the housing 1261 when the reservoir 1264 is the corresponding volume. The user can identify whether the pressure level of the fluid in the reservoir 1264 and a tube portion to which the fluid pressure regulating device 1210 is coupled is, for example, low, medium, or high based on the section of the extending member 1267 that is aligned with the second end 1262B of the housing 1261. Although the extending member 1267 is shown as including three colored indicator sections, the extending member 1267 can include any suitable number of colored indicator sections. Additionally, in some embodiments, rather than colored indicator sections, the extending member 1267 can include any suitable visible markings configured to correspond to particular volumes or volume ranges of the reservoir 1264. For example, the extending member 1267 can include qualitative graduations. In some embodiments, the extending member 1267 can be truncated such that the extending member 1267 only emerges from the cap 1267 through the opening 1267 when the fluid within the reservoir 1264 reaches a critical pressure level. When the user identifies the pressure level as medium and/or high, in some embodiments the user may delay expelling additional fluid into the tube portion coupled to the fluid pressure regulating device 1210 (e.g., delay compressing a syringe plunger) or reduce the rate of expelling additional fluid until the pressure level has dropped and/or may check a system including the fluid pressure regulating device 1210 for obstructions or infiltration.

Figure 15:
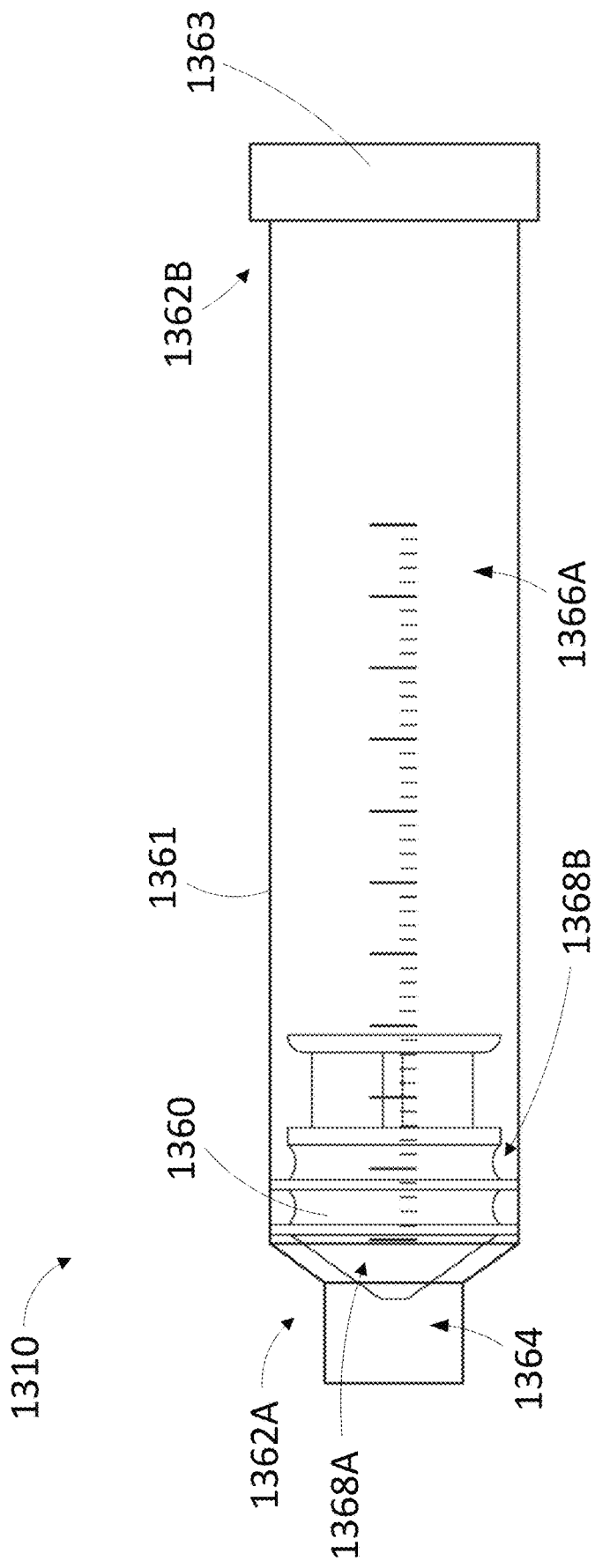
FIG. 15 is a side view of a fluid pressure regulating device, according to an embodiment.

In some embodiments, rather than including a spring member, a fluid pressure regulating device can incorporate an air spring. For example, FIG. 15 is a side view of a fluid pressure regulating device 1310. The fluid pressure regulating device 1310 can be the same or similar in structure and/or function to any of the fluid pressure regulating devices described herein, such as the fluid pressure regulating device 1010 and/or the fluid pressure regulating device 1110. For example, the fluid pressure regulating device 1310 can include a housing 1361 and a seal member 1360. The housing 1361 can define an interior and can have a first end 1362A and a second end 1362B. The first end 1362A of the housing 1361 can be configured to be fluidically coupled to a first tube portion (such as the first tube portion 852 shown in FIG. 10) and a second tube portion (such as the second tube portion 854 shown in FIG. 10) via a fluid connector (such as the fluid connector 853 shown in FIG. 10). The second end 1362B of the housing 1361 includes an end cap 1363. The seal member 1360 can be disposed in the interior of the housing 1361 and can have a first side 1368A and a second side 1368B. The first side 1368A of the seal member 1360 and the housing 1361 can collectively define a first reservoir 1364 having a first volume. The second side 1368B of the seal member 1360 and the housing 1361 can collectively define a second reservoir 1366A having a second volume. The second reservoir 1366A is fluidically isolated from the first reservoir 1364.

The seal member 1360 can be configured to translate within the interior of the housing 1361 such that, when a fluid pressure of a fluid in a lumen of the tube portion fluidically coupled to the reservoir 1364 (e.g., the first tube portion 852 shown in FIG. 10) and the reservoir 1364 increases (e.g., due to the delivery of pressurized fluid from a source of pressurized fluid such as the source of pressurized fluid 830), the fluid applies a force to the seal member 1360 such that the seal member 1360 translates toward the second end 1362B of the housing 1361 and compresses a gas disposed within the second reservoir 1366A such that the volume of the first reservoir 1364 increases as fluid is received into the first reservoir 1364.

In an exemplary embodiment, the inner diameter of the housing 1361 may be between about 0.3" and about 1.5". If the inner diameter of the housing 1361 is too small (e.g., smaller than about 0.3"), the housing 1361 may need to be excessively long to store sufficient fluid. If the inner diameter of the housing 1361 is too large (e.g., greater than about 1.5"), an impractical amount of spring force may be needed to achieve the desired spring rate profile.

The seal member 1360 can be biased toward the first end 1362A of the housing 1361 by the gas in the second reservoir 1366A. Thus, when the fluid pressure of the fluid in the reservoir 1364 decreases, the gas in the second reservoir 1366A expands and applies a force to the seal member 1360 such that fluid is expelled from the first reservoir 1364 as the volume of the first reservoir 1364 decreases.

In some embodiments, any of the systems described herein, such as the system 100, can include a source of pressurized fluid including an infusion device configured to cyclically draw fluid from an assembly (e.g., the fluid source 140) and transfer fluid to a patient. For example, as shown in FIG. 16, a source of pressurized fluid 1430 (e.g., an infusion device) can include a housing 1491 including a grip 1492 and a trigger 1493 coupled to the housing 1491. The source of pressurized fluid 1430 can be the same or similar in structure and/or function to any of the devices described and/or illustrated in International Publication No. WO/2016/138018, such as FIG. 22 of International Publication No. WO/2016/138018. For example, the source of pressurized fluid 1430 can include a shuttle mechanism 1498 disposed within the housing 1491 and mechanically coupled directly or indirectly to the trigger 1493 such that the trigger 1493 can be actuated to linearly translate the shuttle mechanism 1498. As shown in FIG. 16, the housing 1491 and the shuttle mechanism 1498 can be configured to receive a syringe 1494 and a dual check valve assembly 1497. The syringe 1494 can include a syringe barrel 1495 and a plunger 1496. The syringe barrel 1495 can have a first end 1495A and a second end 1495B. The dual check valve assembly 1497 can include a first end 1497A, a second end 1497B, and an inlet 1497C. The second end 1497B of the dual check valve assembly 1497 can be coupled to the first end 1495A of the syringe barrel 1495 such that the interior of the dual check valve assembly 1497 is in fluidic communication with a reservoir defined by the syringe barrel 1495. The dual check valve assembly 1497 can include a first check valve (not shown) disposed within the dual check valve assembly 1497 such that fluid can flow through the inlet 1497C, through the second end 1497B, and into the syringe barrel 1495 (e.g., when the plunger 1496 is drawn relative to the syringe barrel 1495), but fluid is prevented from flowing from the second end 1497B and out of the inlet 1497C. The dual check valve assembly 1497 can include a second check valve (not shown) disposed within the dual check valve assembly 1497 such that fluid can be transferred from the syringe barrel 1495, through the second end 1497B, and through the first end 1497A (e.g., toward the patient), but fluid is prevented from being drawn through the first end (e.g., from the patient) and through the second end 1497B.

In some embodiments, inlet 1497C can be coupled to a fluid source, such as the source of fluid 140, via tubing, such as tubing 142. The first end 1497A of the dual check valve assembly 1497 can be coupled to a patient via patient access tubing (e.g., the tubing portion 152 and the patient access component 120) such that the fluid expelled from the syringe barrel 1495 can be transferred into the patient.

In some embodiments, the source of pressurized fluid 1430 can include a lever (not shown) extending from the trigger 1493 and engaged with the shuttle mechanism 1498. The lever can extend from the trigger and include a cam path. The shuttle mechanism 1498 can be configured to linearly translate the plunger 1496 relative to the syringe barrel 1495 in a first direction to draw fluid through the inlet 1497C and into the syringe barrel 1495 and in a second direction to expel fluid from the syringe barrel 1495 through the second end 1497B and the first end 1497A. Thus, the trigger 1493 can be actuated (e.g., pulled toward the grip 1492) to rotate the lever, causing the shuttle to translate the plunger 1496 in the second direction. The trigger 1493 can then be released, causing the shuttle to translate the plunger 1496 in the first direction.

Figure 18:
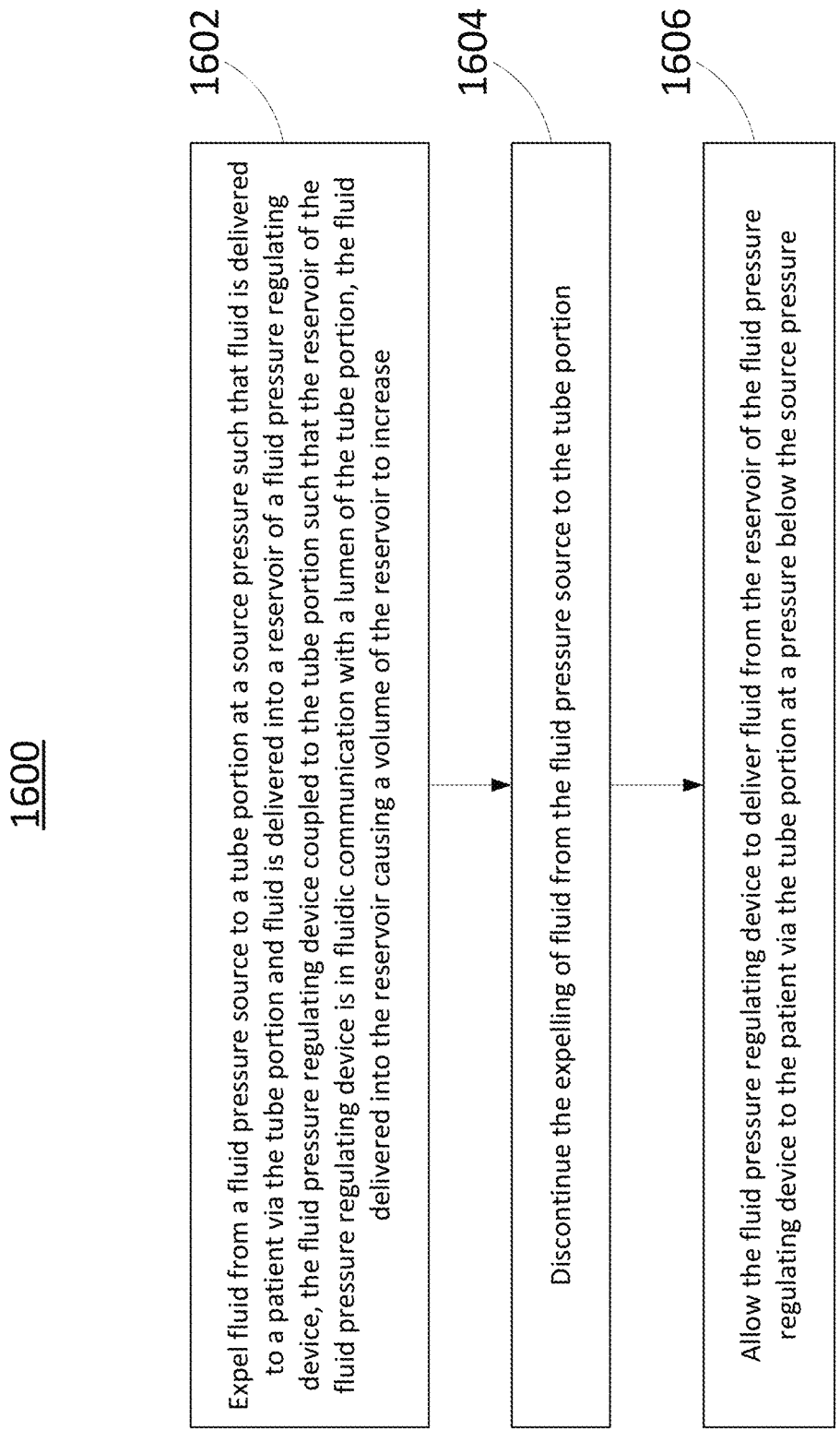
FIG. 18 is a flow chart showing a method, according to an embodiment.

FIG. 18 is a flow chart showing a method 1600, according to an embodiment. The method 1600 can be performed using any suitable system or device, such as any of the systems or devices described herein. The method 1600 includes expelling fluid from a fluid pressure source to a tube portion at a fluid pressure above a threshold pressure (i.e., a source pressure) such that fluid is delivered to a patient via the tube portion and fluid is delivered into a reservoir of a fluid pressure regulating device, at 1602. The fluid pressure regulating device can be coupled to the tube portion such that the reservoir of the fluid pressure regulating device is in fluidic communication with a lumen of the tube portion. The fluid delivered into the reservoir can cause a volume of the reservoir to increase. In some embodiments, expelling fluid from the fluid pressure source can include actuating an actuation mechanism of the fluid pressure source. In some embodiments, expelling fluid from the fluid the fluid pressure source includes translating a plunger of the fluid pressure source toward an outlet of the fluid pressure source, the outlet fluidically coupled to the lumen of the tube portion. The expelling of fluid from the fluid pressure source to the tube portion can be discontinued, at 1604. In some embodiments, discontinuing the expelling of fluid from the fluid pressure source includes releasing an actuation mechanism of the fluid pressure source. At 1606, the fluid pressure regulating device can be allowed to deliver fluid from the reservoir of the fluid pressure regulating device to the patient via the tube portion.

In some embodiments, fluid can be drawn from a fluid source into a reservoir of the fluid pressure source while the fluid pressure regulating device simultaneously delivers fluid from the reservoir of the fluid pressure regulating device to the patient via the tube portion. In some embodiments, drawing fluid from the fluid source can include translating a plunger of the fluid pressure source away from an outlet of the fluid pressure source, the outlet fluidically coupled to the lumen of the tube portion. In some embodiments, after drawing fluid from the fluid source into the reservoir of the fluid pressure source while the fluid pressure regulating device delivers fluid from the reservoir of the fluid pressure regulating device to the patient, fluid can be expelled from the fluid pressure source to the tube portion at the source pressure such that fluid is delivered to the patient via the tube portion and fluid is delivered into the reservoir of the fluid pressure regulating device.

In some embodiments, the volume of the reservoir of the fluid pressure regulating device can transition from a first volume to a second volume greater than the first volume while fluid is expelled from the fluid pressure source to the tube portion, and the volume of the reservoir of the fluid pressure regulating device can transition from the second volume to the first volume while fluid is drawn from the fluid source into the reservoir of the fluid pressure source. In some embodiments, the fluid pressure regulating device and the fluid pressure source can be configured such that the fluid pressure regulating device can transition from the second volume to the first volume within a first time duration or range (e.g., a fluid pressure regulating device expulsion period) and the fluid can be drawn from the fluid source into the reservoir of the fluid pressure source within a second time duration or range (e.g., a refill period). The first time duration or range and the second time duration or range can be substantially similar such that the fluid pressure source is prepared to expel fluid (e.g., a reservoir of the fluid pressure source is full or filled to a threshold volume) when the fluid pressure regulating device reaches the first volume. Thus, refilling the fluid pressure source from the fluid source can have substantially the same time duration as transitioning the fluid pressure regulating device from the second volume to the first volume).

In some embodiments, fluid can be expelled from the fluid pressure source to the tube portion and fluid can be drawn from the fluid source into the reservoir of the fluid pressure source repetitively and serially. While fluid is expelled from the fluid pressure source to the tube portion the volume of the reservoir of the fluid pressure regulating device can transition from a first volume to a second volume greater than the first volume. While fluid is drawn from the fluid source into the reservoir of the fluid pressure source, the volume of the reservoir of the fluid pressure regulating device can transition from the second volume to the first volume.

In some embodiments, expelling fluid from the fluid pressure source can include expelling the fluid at a particular flow rate based on the volume of the reservoir of the fluid pressure regulating device. In some embodiments, for example, expelling fluid from the fluid pressure source to the tube portion can include monitoring the volume of the reservoir and changing the rate of fluid flow from the fluid pressure source based, at least in part, on the volume of the reservoir.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A system, comprising:
a source of pressurized fluid configured to deliver fluid at a source pressure, the source of pressurized fluid including a fluid receptacle and a one-way valve configured such that fluid can flow from the fluid receptacle and through the one-way valve in a first direction and fluid is prevented from flowing in a second direction opposite the first direction through the one-way valve and into the fluid receptacle of the source of pressurized fluid; and
a fluid pressure regulating device including a tube having a first end defining an inlet and a second end defining an outlet, the tube defining a reservoir, the reservoir having a first volume in a first configuration of the tube, the fluid pressure regulating device fluidically coupleable to the source of pressurized fluid such that the source of pressurized fluid is in fluidic communication with the fluid pressure regulating device, the tube configured to expand from the first configuration to a second configuration in which the reservoir has a second volume greater than the first volume when a pressure of fluid within the reservoir increases, the tube being resiliently biased toward the first configuration, the fluid pressure regulating device configured to deliver fluid having a pulsatile flow rate from the reservoir of the tube via the outlet,
the tube configured such that, in the first configuration of the tube, fluid can flow from the source of pressurized fluid to a patient by flowing through the inlet of the tube and into contact with an inner wall of the tube, flowing along and in contact with the inner wall of the tube from the first end of the tube to the second end of the tube, and flowing from the second end of the tube through the outlet of the tube, the fluid pressure regulating device configured such that, when fluid is delivered from the fluid receptacle of the source of pressurized fluid through the inlet of the first end of the tube to the reservoir of the tube at the source pressure, the reservoir of the tube receives fluid such that the tube expands from the first configuration to the second configuration and fluid is delivered from the reservoir of the tube through the outlet of the second end of the tube.

2. The system of claim 1, further comprising a tube portion having a first end, a second end, and defining a lumen extending from the first end to the second end, the first end of the tube portion coupleable to the source of pressurized fluid and the second end of the tube portion coupleable to the fluid pressure regulating device such that fluid can be delivered from the source of pressurized fluid to reservoir of the tube of the fluid pressure regulating device via the tube portion.

3. The system of claim 2, wherein the tube portion is a first tube portion and further comprising:

a second tube portion having a first end and a second end and defining a lumen extending from the first end to the second end, the first end of the second tube portion coupled to the fluid pressure regulating device and the second end of the second tube portion configured to be coupled to a patient access component such that fluid delivered from the reservoir of the tube through the second end of the tube can be delivered to the patient via the second tube portion and the patient access component.

4. The system of claim 3, wherein the patient access component includes at least one of a catheter, a needle, or a port.

5. The system of claim 1, wherein the tube is an inner tube and the fluid pressure regulating device includes an outer tube, the outer tube having a first end and a second end and defining a lumen, the outer tube being expandable from a first configuration to a second configuration, the outer tube being resiliently biased toward the first configuration; and the inner tube disposed within the lumen of the outer tube, the first end of the inner tube coupled to the first end of the outer tube via a first end connector, the second end of the inner tube coupled to the second end of the outer tube via a second end connector, the inner tube configured to apply a force on the outer tube while transitioning from the first configuration of the inner tube to the second configuration of the inner tube to cause the outer tube to expand from the first configuration of the outer tube to the second configuration of the outer tube.

6. The system of claim 1, wherein the reservoir is cylindrical in the first configuration of the tube.

7. The system of claim 1, wherein a length from the first end to the second end of the tube is the same in the first configuration and the second configuration of the tube.

8. The system of claim 1, wherein the source of pressurized fluid includes a reciprocating actuator configured to deliver a discrete volume of fluid from the fluid receptacle of the source of pressurized fluid with each cycle of the reciprocating actuator.

9. The system of claim 1, wherein the fluid pressure regulating device is configured such that, when the source of pressurized fluid is not delivering fluid to the reservoir of the tube of the fluid pressure regulating device and the reservoir of the tube of the fluid pressure regulating device has a volume greater than the first volume, the reservoir can decrease in size due to the tube being resiliently biased toward the first configuration to deliver fluid from the reservoir through the second end of the tube.

10. The system of claim 2, wherein the source of pressurized fluid is configured to alternate between an expulsion state in which the source of pressurized fluid expels fluid from the fluid receptacle of the source of pressurized fluid into the lumen of the tube portion and a drawing state in which the source of pressurized fluid draws fluid from a fluid source into the fluid receptacle of the source of pressurized fluid, the system being configured to deliver fluid from the second end of the tube of the fluid pressure regulating device during both the expulsion state and the drawing state of the source of pressurized fluid.

11. The system of claim 1, wherein an inner diameter of the tube in the first configuration is sufficiently small such that no air will be trapped in the reservoir during priming of the fluid pressure regulating device regardless of the orientation of the tube during priming.

12. A method, comprising:

expelling fluid from a source of pressurized fluid to a tube portion via a fluid pressure regulating device at a source pressure such that fluid is delivered through an inlet of the fluid pressure regulating device and into a reservoir of the fluid pressure regulating device and is delivered to a patient from the reservoir through an outlet of the fluid pressure regulating device and the tube portion at a first instantaneous flow rate, the fluid pressure regulating device including a tube having a first end defining the inlet, having a second end defining the outlet, and defining the reservoir, the fluid delivered into the reservoir causing the tube to transition from a first configuration having a first volume to a second configuration having a second volume greater than the first volume, the tube configured such that, in the first configuration of the tube, fluid can flow from the source of pressurized fluid to the patient by flowing through the inlet of the tube and into contact with an inner wall of the tube, flowing along and in contact with the inner wall of the tube from the first end of the tube to the second end of the tube, and flowing from the second end of the tube through the outlet of the tube;

discontinuing the expelling of fluid from the source of pressurized fluid; and allowing the fluid pressure regulating device to deliver fluid from the reservoir and through the outlet of the fluid pressure regulating device to the patient via the tube portion at a second instantaneous flow rate lower than the first instantaneous flow rate.

13. The method of claim 12, further comprising:

drawing fluid from a fluid source into a fluid receptacle of the source of pressurized fluid while the fluid pressure regulating device delivers fluid from the reservoir of the fluid pressure regulating device to the patient via the tube portion.

14. The method of claim 13, further comprising, after drawing fluid from the fluid source into the fluid receptacle of the source of pressurized fluid while the fluid pressure regulating device delivers fluid from the reservoir of the fluid pressure regulating device to the patient, expelling fluid from the source of pressurized fluid to the tube portion via the fluid pressure regulating device at the source pressure such that fluid is delivered to the patient via the tube portion and fluid is delivered into the reservoir of the fluid pressure regulating device.

15. The method of claim 13, wherein the volume of the reservoir of the fluid pressure regulating device transitions from the first volume to the second volume while fluid is expelled from the source of pressurized fluid to the tube portion, and the volume of the reservoir of the fluid pressure regulating device transitions from the second volume to the first volume while fluid is drawn from the fluid source into the fluid receptacle of the source of pressurized fluid.

16. The method of claim 13, wherein the expelling of the fluid from the source of pressurized fluid and the drawing fluid from the fluid source into the fluid receptacle occur simultaneously.

17. The method of claim 12, wherein expelling fluid from the source of pressurized fluid includes actuating an actuation mechanism of the source of pressurized fluid.

18. The method of claim 12, wherein discontinuing the expelling of fluid from the source of pressurized fluid includes releasing an actuation mechanism of the source of pressurized fluid.

19. The method of claim 12, wherein the expelling the fluid from the source of pressurized fluid includes actuating an actuation mechanism of the source of pressurized fluid by hand.

20. The method of claim 19, wherein the actuating the actuation mechanism by hand includes feeling tactile feedback that corresponds to a pressure of fluid within the fluid pressure regulating device.

* * * * *